(12) United States Patent
Choi et al.

(10) Patent No.: US 9,044,397 B2
(45) Date of Patent: Jun. 2, 2015

(54) MEDICAL DEVICES WITH GALVANIC PARTICULATES

(71) Applicant: Ethicon, Inc., Somerville, NJ (US)

(72) Inventors: Jennifer Hagyoung Kang Choi, Metuchen, NJ (US); Chunlin Yang, Belle Mead, NJ (US); Ying Sun, Belle Mead, NJ (US); Carrie H. Fang, Pittstown, NJ (US); James E. Hauschild, Cranbury, NJ (US); Abla A. Creasey, Morristown, NJ (US)

(73) Assignee: Ethicon, Inc., Somerville, NJ (US)

( * ) Notice: Subject to any disclaimer, the term of this patent is extended or adjusted under 35 U.S.C. 154(b) by 24 days.

(21) Appl. No.: 13/937,363

(22) Filed: Jul. 9, 2013

(65) Prior Publication Data

US 2013/0295184 A1 Nov. 7, 2013

Related U.S. Application Data

(60) Division of application No. 13/207,398, filed on Aug. 10, 2011, now abandoned, which is a continuation-in-part of application No. 12/890,881, filed on Sep. 27, 2010, now abandoned, and a continuation-in-part of application No. 12/761,601, filed on Apr. 16, 2010, now abandoned, and a continuation-in-part of application No. 12/731,848, filed on Mar. 25, 2010, now abandoned.

(60) Provisional application No. 61/163,928, filed on Mar. 27, 2009.

(51) Int. Cl.
| | |
|---|---|
| *A61K 33/30* | (2006.01) |
| *A61K 33/34* | (2006.01) |
| *A61K 33/38* | (2006.01) |
| *A61K 9/14* | (2006.01) |
| *A61L 15/18* | (2006.01) |
| *A61L 15/42* | (2006.01) |
| *A61L 26/00* | (2006.01) |
| *A61L 27/24* | (2006.01) |
| *A61L 27/30* | (2006.01) |
| *A61L 27/50* | (2006.01) |
| *A61L 27/54* | (2006.01) |
| *A61L 29/10* | (2006.01) |
| *A61L 29/14* | (2006.01) |
| *A61L 31/08* | (2006.01) |
| *A61L 31/14* | (2006.01) |
| *A61K 33/06* | (2006.01) |

(52) U.S. Cl.
CPC ............ *A61K 9/143* (2013.01); *A61L 15/18* (2013.01); *A61L 15/42* (2013.01); *A61L 26/0004* (2013.01); *A61L 26/0066* (2013.01); *A61L 27/24* (2013.01); *A61L 27/30* (2013.01); *A61L 27/306* (2013.01); *A61L 27/50* (2013.01); *A61L 27/54* (2013.01); *A61L 29/106* (2013.01); *A61L 29/14* (2013.01); *A61L 31/088* (2013.01); *A61L 31/14* (2013.01); *A61L 2300/102* (2013.01); *A61L 2300/104* (2013.01); *A61L 2300/402* (2013.01); *A61L 2300/404* (2013.01); *A61L 2300/41* (2013.01); *A61L 2300/414* (2013.01); *A61L 2300/45* (2013.01); *A61L 2300/622* (2013.01); *A61K 33/06* (2013.01); *A61K 33/30* (2013.01); *A61K 33/34* (2013.01); *A61K 33/38* (2013.01)

(58) Field of Classification Search
None
See application file for complete search history.

(56) References Cited

U.S. PATENT DOCUMENTS

| | | | |
|---|---|---|---|
| 3,767,783 | A | 10/1973 | Lung |
| 3,871,906 | A | 3/1975 | Sweeny |
| 3,957,452 | A | 5/1976 | Schaer |
| 3,981,747 | A | 9/1976 | Doniat |
| 4,067,342 | A | 1/1978 | Burton |
| 4,123,511 | A | 10/1978 | Heintze |
| 4,167,416 | A | 9/1979 | Zolla |
| 4,211,222 | A | 7/1980 | Tapper |
| 4,223,661 | A | 9/1980 | Sergev |
| 4,305,390 | A | 12/1981 | Swartz |
| 4,372,296 | A | 2/1983 | Fahim |
| 4,406,658 | A | 9/1983 | Lattin |

(Continued)

FOREIGN PATENT DOCUMENTS

| | | |
|---|---|---|
| DE | 19831798 A1 | 1/2000 |
| EP | 337642 A2 | 10/1989 |

(Continued)

OTHER PUBLICATIONS

Anonymous: "Zinc dust XL—Premium Data Sheet", US Zinc Products, Oct. 20, 2003, XP002661863, Retrieved from the Internet: URL:http://www.uszinc.com/en-US/zincdust/Documents/Pdf/XLPremiumTypeIII.pdf.

(Continued)

*Primary Examiner* — H. Sarah Park

(57) ABSTRACT

Implantable medical devices having galvanic particulates are disclosed. The particulate may be coated onto at least part of a surface of the medical device. In addition, the galvanic particulates may be contained in the material used to manufacture the antimicrobial medical devices, or may be embedded into the surface of the medical devices. The present invention also provides novel coating methods and processing methods. The present invention further provides a combination of galvanic particulates with an aqueous gel, a method of making this combination, and a method of treatment using this combination. The devices and compositions may have advantageous characteristics and effects including anti-microbial, anti-inflammatory, tissue regeneration promoting, and pain reduction or elimination.

3 Claims, 8 Drawing Sheets

(56) References Cited

U.S. PATENT DOCUMENTS

| | | |
|---|---|---|
| 4,431,500 A | 2/1984 | Messing |
| 4,456,474 A | 6/1984 | Jost |
| 4,474,570 A | 10/1984 | Ariura |
| 4,606,354 A * | 8/1986 | Jacob .......................... 607/116 |
| 4,665,054 A | 5/1987 | Pickart |
| 4,689,039 A | 8/1987 | Masaki |
| 4,760,051 A | 7/1988 | Pickart |
| 4,764,164 A | 8/1988 | Sasaki |
| 4,767,401 A | 8/1988 | Seiderman |
| 4,795,631 A | 1/1989 | Sheehan |
| 4,810,693 A | 3/1989 | Pickart |
| 4,842,477 A | 6/1989 | Stowell |
| 4,842,577 A | 6/1989 | Konno |
| 4,852,571 A | 8/1989 | Gadsby |
| 4,877,770 A | 10/1989 | Pickart |
| 4,895,727 A | 1/1990 | Allen |
| 4,921,583 A | 5/1990 | Sewell |
| 4,956,184 A | 9/1990 | Kross |
| 4,957,480 A | 9/1990 | Morenings |
| 4,970,252 A | 11/1990 | Sakuta |
| 4,979,938 A | 12/1990 | Stephen |
| 5,042,975 A | 8/1991 | Chien |
| 5,084,006 A | 1/1992 | Lew |
| 5,122,418 A | 6/1992 | Nakane |
| 5,135,913 A | 8/1992 | Pickart |
| 5,147,297 A | 9/1992 | Myers |
| 5,162,043 A | 11/1992 | Lew |
| 5,224,927 A | 7/1993 | Tapper |
| 5,231,169 A | 7/1993 | Constantz |
| 5,298,017 A | 3/1994 | Theeuwes |
| 5,304,403 A | 4/1994 | Schlesinger |
| 5,314,502 A | 5/1994 | McNichols |
| 5,322,520 A | 6/1994 | Milder |
| 5,326,341 A | 7/1994 | Lew |
| 5,338,412 A | 8/1994 | Burk |
| 5,348,943 A | 9/1994 | Pickart |
| 5,352,315 A | 10/1994 | Carrier |
| 5,356,632 A | 10/1994 | Gross |
| 5,380,272 A | 1/1995 | Gross |
| 5,382,431 A | 1/1995 | Pickart |
| 5,384,134 A | 1/1995 | Kross |
| 5,387,189 A | 2/1995 | Gory |
| 5,389,220 A | 2/1995 | Herzog |
| 5,405,317 A | 4/1995 | Myers |
| 5,412,004 A | 5/1995 | Tachibana |
| 5,415,628 A | 5/1995 | Untereker |
| 5,416,364 A | 5/1995 | Divjak |
| 5,428,185 A | 6/1995 | Kunimoto |
| 5,443,441 A | 8/1995 | De Claviere |
| 5,466,217 A | 11/1995 | Myers |
| 5,470,349 A | 11/1995 | Kleditsch |
| 5,487,884 A | 1/1996 | Bissett |
| 5,498,248 A | 3/1996 | Milder |
| 5,503,840 A | 4/1996 | Jacobson |
| 5,505,949 A | 4/1996 | Benitez |
| 5,550,183 A | 8/1996 | Pickart |
| 5,589,256 A | 12/1996 | Hansen |
| 5,595,750 A | 1/1997 | Jacobson |
| 5,601,750 A | 2/1997 | Domke |
| 5,624,415 A | 4/1997 | Cormier |
| 5,624,425 A | 4/1997 | Gray |
| 5,637,084 A | 6/1997 | Kontturi |
| 5,648,389 A | 7/1997 | Gans |
| 5,653,989 A | 8/1997 | Sattler |
| 5,654,362 A | 8/1997 | Schulz, Jr. |
| 5,670,468 A | 9/1997 | Moens |
| 5,678,545 A | 10/1997 | Stratbucker |
| 5,685,837 A | 11/1997 | Horstmann |
| 5,688,233 A | 11/1997 | Hofmann |
| 5,759,564 A | 6/1998 | Milder |
| 5,760,116 A | 6/1998 | Kilgour |
| 5,811,487 A | 9/1998 | Schulz, Jr. |
| 5,817,044 A | 10/1998 | Evers |
| 5,830,175 A | 11/1998 | Flower |
| 5,834,899 A | 11/1998 | Lovell |
| 5,843,186 A | 12/1998 | Christ |
| 5,855,570 A | 1/1999 | Scherson |
| 5,897,522 A | 4/1999 | Nitzan |
| 5,928,185 A | 7/1999 | Muller |
| 5,931,996 A | 8/1999 | Reisser |
| 5,935,598 A | 8/1999 | Sage |
| 5,955,017 A | 9/1999 | Foffano |
| 5,955,067 A | 9/1999 | Oge |
| 5,961,483 A | 10/1999 | Sage |
| 5,964,936 A | 10/1999 | Reisser |
| 5,974,344 A | 10/1999 | Shoemaker, II |
| 5,985,308 A | 11/1999 | Burrell |
| 5,993,435 A | 11/1999 | Haak |
| 5,993,526 A | 11/1999 | Sommer |
| 6,004,309 A | 12/1999 | Phipps |
| 6,017,553 A | 1/2000 | Burrell |
| 6,038,485 A | 3/2000 | Axelgaard |
| 6,045,570 A | 4/2000 | Epstein |
| 6,060,000 A | 5/2000 | Milder |
| 6,078,842 A | 6/2000 | Gross |
| 6,104,950 A | 8/2000 | Higo |
| 6,113,636 A | 9/2000 | Ogle |
| 6,120,756 A | 9/2000 | Markowitz |
| 6,157,858 A | 12/2000 | Gross |
| 6,169,920 B1 | 1/2001 | Haak |
| 6,185,453 B1 | 2/2001 | Hussain |
| 6,218,350 B1 | 4/2001 | Beggs |
| 6,223,076 B1 | 4/2001 | Tapper |
| 6,231,830 B1 | 5/2001 | Madray |
| 6,238,381 B1 | 5/2001 | Tapper |
| 6,241,561 B1 | 6/2001 | Zebermann |
| 6,248,449 B1 | 6/2001 | Watanabe |
| RE37,263 E | 7/2001 | Kross |
| 6,273,875 B1 | 8/2001 | Siman |
| 6,275,372 B1 | 8/2001 | Vassallo |
| 6,287,484 B1 | 9/2001 | Hausslein |
| 6,289,241 B1 | 9/2001 | Phipps |
| 6,294,186 B1 | 9/2001 | Beerse |
| 6,302,874 B1 | 10/2001 | Zhang |
| 6,306,384 B1 | 10/2001 | Lahanas |
| 6,317,629 B1 | 11/2001 | Haak |
| 6,322,588 B1 | 11/2001 | Ogle |
| 6,383,523 B1 | 5/2002 | Murad |
| 6,385,487 B1 | 5/2002 | Henley |
| 6,410,062 B1 | 6/2002 | Callaghan |
| 6,421,561 B1 | 7/2002 | Morris |
| 6,424,862 B1 | 7/2002 | Brown, III |
| 6,443,978 B1 | 9/2002 | Zharov |
| 6,444,212 B1 | 9/2002 | Cavazzuti |
| 6,455,065 B1 | 9/2002 | Hymes |
| 6,475,472 B2 | 11/2002 | Joiner |
| 6,488,965 B1 | 12/2002 | Karageozian |
| 6,494,900 B1 | 12/2002 | Salansky |
| 6,495,158 B1 | 12/2002 | Buseman |
| 6,522,918 B1 | 2/2003 | Crisp |
| 6,544,401 B1 | 4/2003 | Colic |
| 6,552,895 B1 | 4/2003 | Vassallo |
| 6,560,483 B1 | 5/2003 | Kumar |
| 6,582,416 B2 | 6/2003 | Tapper |
| 6,584,349 B1 | 6/2003 | Sage, Jr. |
| 6,605,751 B1 | 8/2003 | Gibbins |
| 6,629,947 B1 | 10/2003 | Sahatjian |
| 6,631,294 B2 | 10/2003 | Andino |
| 6,632,342 B1 | 10/2003 | Teshima |
| 6,653,014 B2 | 11/2003 | Anderson |
| 6,654,635 B1 | 11/2003 | Koga |
| 6,673,374 B2 | 1/2004 | Murad |
| 6,708,050 B2 | 3/2004 | Carim |
| 6,734,155 B1 | 5/2004 | Herbots |
| 6,735,470 B2 | 5/2004 | Henley |
| 6,738,662 B1 | 5/2004 | Frank |
| 6,745,071 B1 | 6/2004 | Grace |
| 6,766,022 B1 | 7/2004 | Bartolutti |
| 6,766,202 B2 | 7/2004 | Underwood |
| 6,775,570 B2 | 8/2004 | Joshi |
| 6,818,212 B2 | 11/2004 | Johansen |
| 6,821,281 B2 | 11/2004 | Sherman |
| 6,821,333 B2 | 11/2004 | Zimmermann |
| 6,855,117 B2 | 2/2005 | Skover |

(56) References Cited

U.S. PATENT DOCUMENTS

| | | |
|---|---|---|
| 6,866,856 B2 | 3/2005 | Lu |
| 6,890,553 B1 | 5/2005 | Sun |
| 6,989,156 B2 | 1/2006 | Gillis |
| 7,005,408 B2 | 2/2006 | Ahmad |
| 7,008,647 B2 | 3/2006 | Burrell |
| 7,018,660 B2 | 3/2006 | Murad |
| 7,172,812 B2 | 2/2007 | Greiwe |
| 7,177,693 B2 | 2/2007 | Starkebaum |
| 7,220,316 B2 | 5/2007 | Kitsuwa |
| 7,233,017 B2 | 6/2007 | Yoon |
| 7,271,199 B1 | 9/2007 | Quinn |
| 7,332,246 B2 | 2/2008 | Wiepen |
| 7,387,807 B2 | 6/2008 | Callaghan |
| 7,457,667 B2 | 11/2008 | Skiba |
| 7,459,667 B1 | 12/2008 | Lee |
| 7,476,221 B2 | 1/2009 | Sun |
| 7,476,222 B2 | 1/2009 | Sun |
| 7,477,938 B2 | 1/2009 | Sun |
| 7,477,939 B2 | 1/2009 | Sun |
| 7,477,940 B2 | 1/2009 | Sun |
| 7,477,941 B2 | 1/2009 | Sun |
| 7,479,133 B2 | 1/2009 | Sun |
| 7,480,530 B2 | 1/2009 | Sun |
| 7,486,989 B2 | 2/2009 | Sun |
| 7,495,146 B2 | 2/2009 | Crisp |
| 7,507,228 B2 | 3/2009 | Sun |
| 7,507,285 B2 | 3/2009 | Venturini |
| 7,666,803 B2 | 2/2010 | Shetty |
| 8,025,673 B1 | 9/2011 | Lyapko |
| 8,150,525 B2 | 4/2012 | Fassih |
| 8,196,461 B2 | 6/2012 | Abraham |
| 8,239,017 B2 | 8/2012 | Sun |
| 2001/0012510 A1 | 8/2001 | Fishman |
| 2002/0082694 A1 | 6/2002 | McKay |
| 2002/0099320 A1 | 7/2002 | Beck |
| 2002/0173743 A1 | 11/2002 | Tapper |
| 2002/0173833 A1 | 11/2002 | Korman |
| 2002/0182485 A1 | 12/2002 | Anderson |
| 2002/0183685 A1 | 12/2002 | Crawford |
| 2002/0188241 A1 | 12/2002 | Morris |
| 2002/0188942 A1 | 12/2002 | Bryan et al. |
| 2003/0019501 A1 | 1/2003 | Hirota |
| 2003/0023270 A1 | 1/2003 | Danz |
| 2003/0028170 A1 | 2/2003 | Anderson |
| 2003/0035955 A1 | 2/2003 | Yadav |
| 2003/0039860 A1 | 2/2003 | Cheon |
| 2003/0049536 A1 | 3/2003 | Wiepen |
| 2003/0054046 A1 | 3/2003 | Burrell |
| 2003/0059673 A1 | 3/2003 | Langan |
| 2003/0100884 A1 | 5/2003 | Deagle |
| 2003/0108612 A1 | 6/2003 | Xu |
| 2003/0149393 A1 | 8/2003 | Joshi |
| 2003/0176832 A1 | 9/2003 | Rossi |
| 2003/0216783 A1 | 11/2003 | Lehtoluoto |
| 2004/0006374 A1 | 1/2004 | Mondin |
| 2004/0043062 A1 | 3/2004 | Sun |
| 2004/0044384 A1 | 3/2004 | Leber |
| 2004/0086474 A1 | 5/2004 | Rabe |
| 2004/0110738 A1 | 6/2004 | Gillis |
| 2004/0115239 A1 | 6/2004 | Shastri |
| 2004/0138712 A1 | 7/2004 | Tamarkin |
| 2004/0167460 A1 | 8/2004 | Anderson |
| 2004/0167461 A1 | 8/2004 | Nitzan |
| 2004/0208902 A1 | 10/2004 | Gupta |
| 2004/0213820 A1 | 10/2004 | Yokoi |
| 2004/0219124 A1 | 11/2004 | Gupta |
| 2004/0223932 A1 | 11/2004 | Hedgpeth |
| 2004/0265395 A1 | 12/2004 | Sun |
| 2004/0267169 A1 | 12/2004 | Sun |
| 2004/0267189 A1 | 12/2004 | Mavor |
| 2004/0267190 A1 | 12/2004 | Tamarkin |
| 2004/0267231 A1 | 12/2004 | Sun |
| 2004/0267232 A1 | 12/2004 | Sun |
| 2004/0267236 A1 | 12/2004 | Sun |
| 2004/0267237 A1 | 12/2004 | Sun |
| 2005/0004508 A1 | 1/2005 | Sun |
| 2005/0004509 A1 | 1/2005 | Sun |
| 2005/0004550 A1 | 1/2005 | Sun |
| 2005/0008861 A1 | 1/2005 | Yadav |
| 2005/0010161 A1 | 1/2005 | Sun |
| 2005/0010192 A1 | 1/2005 | Sun |
| 2005/0015042 A1 | 1/2005 | Sun |
| 2005/0064176 A1 | 3/2005 | Terry |
| 2005/0112759 A1 | 5/2005 | Radisic |
| 2005/0123620 A1 | 6/2005 | Chiou |
| 2005/0126338 A1 | 6/2005 | Yadav |
| 2005/0148996 A1 | 7/2005 | Sun |
| 2005/0175649 A1 | 8/2005 | Disalvo |
| 2005/0186151 A1 | 8/2005 | Giroud |
| 2005/0187580 A1 | 8/2005 | Skiba |
| 2006/0015052 A1 | 1/2006 | Crisp |
| 2006/0015053 A1 | 1/2006 | Crisp |
| 2006/0024338 A1 | 2/2006 | Hegedus |
| 2006/0042509 A1 | 3/2006 | Henglein |
| 2006/0084338 A1 | 4/2006 | Shetty |
| 2006/0110415 A1 | 5/2006 | Gupta |
| 2006/0133134 A1 | 6/2006 | Doyle |
| 2006/0159643 A1 | 7/2006 | Jacquier |
| 2006/0204581 A1 | 9/2006 | Gower |
| 2006/0222595 A1 | 10/2006 | Mukherjee |
| 2006/0229711 A1 | 10/2006 | Yan |
| 2006/0233869 A1 | 10/2006 | Looney et al. |
| 2006/0263308 A1 | 11/2006 | Brown |
| 2006/0264804 A1 | 11/2006 | Karmon |
| 2007/0003516 A1 | 1/2007 | Almond |
| 2007/0060862 A1 | 3/2007 | Sun |
| 2007/0065392 A1 | 3/2007 | Simonnet |
| 2007/0077312 A1 | 4/2007 | Berchert |
| 2007/0092462 A1 | 4/2007 | Gans Russ |
| 2007/0122461 A1 | 5/2007 | Ko |
| 2007/0128137 A1 | 6/2007 | Yoshimi et al. |
| 2007/0141173 A1 | 6/2007 | Miyamoto |
| 2007/0172438 A1 | 7/2007 | Kruger |
| 2007/0182438 A1 | 8/2007 | Khandros |
| 2007/0185541 A1 | 8/2007 | DiUbaldi |
| 2007/0191756 A1 | 8/2007 | Tapper |
| 2007/0203534 A1 | 8/2007 | Tapper |
| 2007/0207335 A1 | 9/2007 | Karandikar |
| 2007/0219606 A1 | 9/2007 | Moreci |
| 2007/0239212 A1 | 10/2007 | Schneider et al. |
| 2007/0270942 A1 | 11/2007 | Thomas |
| 2008/0014247 A1 | 1/2008 | Lu |
| 2008/0038216 A1 | 2/2008 | Zukowski |
| 2008/0039770 A1 | 2/2008 | Francis |
| 2008/0050448 A1 | 2/2008 | Wilson |
| 2008/0050452 A1 | 2/2008 | Chen |
| 2008/0125838 A1 | 5/2008 | Francis |
| 2008/0127990 A1 | 6/2008 | Thevenet |
| 2008/0199352 A1 | 8/2008 | Fuller |
| 2008/0241262 A1 | 10/2008 | Lee et al. |
| 2008/0249638 A1 | 10/2008 | Asgari |
| 2008/0254147 A1 | 10/2008 | Huey |
| 2008/0311165 A1 | 12/2008 | Gabbay |
| 2008/0312579 A1 | 12/2008 | Chang |
| 2009/0035342 A1 | 2/2009 | Karandikar |
| 2009/0039775 A1 | 2/2009 | Tomai |
| 2009/0045720 A1 | 2/2009 | Lee |
| 2009/0076479 A1 | 3/2009 | Sun |
| 2009/0123733 A1 | 5/2009 | Ohrlander |
| 2009/0149426 A1 | 6/2009 | Lee |
| 2009/0292328 A1 | 11/2009 | Birkill |
| 2009/0304811 A1 | 12/2009 | Xia |
| 2010/0034767 A1 | 2/2010 | Trabelsi |
| 2010/0057147 A1 | 3/2010 | Fassih |
| 2010/0082088 A1 | 4/2010 | Fassih |
| 2010/0092408 A1 | 4/2010 | Breyfogle |
| 2010/0209515 A1 | 8/2010 | Chantalat |
| 2010/0209525 A1 | 8/2010 | Bohmer |
| 2010/0249927 A1 | 9/2010 | Yang |
| 2010/0268335 A1 | 10/2010 | Yang |
| 2011/0060419 A1 | 3/2011 | Choi |
| 2011/0118655 A1 | 5/2011 | Fassih |
| 2011/0172724 A1 | 7/2011 | Hort |
| 2011/0195100 A1 | 8/2011 | Bruning |

(56) References Cited

U.S. PATENT DOCUMENTS

| | | |
|---|---|---|
| 2011/0212042 A1 | 9/2011 | Maitra |
| 2011/0236491 A1 | 9/2011 | Chantalat |
| 2011/0287075 A1 | 11/2011 | Chantalat |
| 2011/0288026 A1 | 11/2011 | Simpson |
| 2012/0015048 A1 | 1/2012 | Maitra |
| 2012/0021014 A1 | 1/2012 | Chantalat |
| 2012/0089232 A1 | 4/2012 | Choi |
| 2012/0148633 A1 | 6/2012 | Sun |
| 2013/0254401 A1 | 9/2013 | Marshall et al. |

FOREIGN PATENT DOCUMENTS

| | | |
|---|---|---|
| EP | 532451 A1 | 3/1993 |
| EP | 800382 A1 | 10/1997 |
| EP | 11060417 A | 3/1999 |
| EP | 1008365 A1 | 6/2000 |
| EP | 1249222 A1 | 10/2002 |
| EP | 1484012 A1 | 12/2004 |
| EP | 1315536 B1 | 11/2007 |
| EP | 14677843 B1 | 8/2008 |
| EP | 1990377 A1 | 11/2008 |
| EP | 1513491 B1 | 2/2009 |
| EP | 1291939 B1 | 3/2009 |
| EP | 2353578 A2 | 8/2011 |
| FR | 2932983 | 1/2010 |
| GB | 1270410 A | 4/1972 |
| GB | 2206493 A | 1/1989 |
| JP | 61018708 A | 1/1986 |
| JP | 3080874 A | 4/1991 |
| JP | 7233017 A | 9/1995 |
| JP | 8196461 A | 8/1996 |
| JP | 10024108 A | 1/1998 |
| JP | 03080874 B2 | 8/2000 |
| JP | 2008069097 A | 3/2008 |
| RU | 45627 U1 | 5/2005 |
| WO | WO8901764 A1 | 3/1989 |
| WO | WO9116034 A1 | 10/1991 |
| WO | WO9116035 A1 | 10/1991 |
| WO | WO9300959 A1 | 1/1993 |
| WO | WO9314813 A1 | 8/1993 |
| WO | WO9411058 A1 | 5/1994 |
| WO | WO 9411058 A1 | 5/1994 |
| WO | WO9416765 A1 | 8/1994 |
| WO | WO9417853 A1 | 8/1994 |
| WO | WO 9523588 A1 | 9/1995 |
| WO | WO9706847 A1 | 2/1997 |
| WO | WO9814237 A1 | 4/1998 |
| WO | WO9829158 A1 | 7/1998 |
| WO | WO 9920229 A1 | 4/1999 |
| WO | WO9943382 A1 | 9/1999 |
| WO | WO9956819 A1 | 11/1999 |
| WO | WO0007658 A1 | 2/2000 |
| WO | WO0012173 A1 | 3/2000 |
| WO | WO 0037071 A1 | 6/2000 |
| WO | WO0047274 A1 | 8/2000 |
| WO | WO0062587 A1 | 10/2000 |
| WO | WO0062856 A1 | 10/2000 |
| WO | WO0074695 A2 | 12/2000 |
| WO | WO0074772 A1 | 12/2000 |
| WO | WO0180945 A1 | 11/2001 |
| WO | WO 0209216 A2 | 1/2002 |
| WO | WO02098502 A2 | 12/2002 |
| WO | WO03032959 A1 | 4/2003 |
| WO | WO03066016 A1 | 8/2003 |
| WO | WO 03066156 A2 | 8/2003 |
| WO | WO03082095 A1 | 10/2003 |
| WO | WO 2004/105865 | 12/2004 |
| WO | WO 2005004979 A1 | 1/2005 |
| WO | WO2005004979 A1 | 1/2005 |
| WO | WO2005004981 A2 | 1/2005 |
| WO | WO 2005004981 A2 | 1/2005 |
| WO | WO 2005004982 A2 | 1/2005 |
| WO | WO2005004982 A2 | 1/2005 |
| WO | WO 2005004983 A2 | 1/2005 |
| WO | WO 2005004984 A1 | 1/2005 |
| WO | WO2005004984 A1 | 1/2005 |
| WO | WO2005023206 A2 | 3/2005 |
| WO | WO 2005079913 A1 | 9/2005 |
| WO | WO2006048879 A1 | 5/2006 |
| WO | WO2006056984 A2 | 6/2006 |
| WO | WO2006072834 A2 | 7/2006 |
| WO | WO2006133134 A2 | 12/2006 |
| WO | WO20067003516 A2 | 1/2007 |
| WO | WO2007048772 A1 | 5/2007 |
| WO | WO2008019116 A2 | 2/2008 |
| WO | WO2008079898 A1 | 7/2008 |
| WO | WO 2009045720 A2 | 4/2009 |
| WO | WO2009045720 A2 | 4/2009 |
| WO | WO 2009045720 A2 * | 4/2009 |
| WO | WO 2009045750 A1 | 4/2009 |
| WO | WO2010027792 A1 | 3/2010 |
| WO | WO 2010051918 A2 | 5/2010 |
| WO | WO2010111502 A2 | 9/2010 |
| WO | WO2010111511 A1 | 9/2010 |
| WO | WO2011059915 A1 | 5/2011 |

OTHER PUBLICATIONS

ASM International Handbook: Powder Metal Technologies and Applications, 1998, vol. 7, pp. 31-109, 311-320.
Bajzer, M. et al., Obesity and Gut Flora, Nature, vol. 444, Dec. 21/28, 2006, p. 1009-1010.
Barrow, G.M., "The Electromotive Force of Chemical Cells", Physical Chemistry, Fourth Edition, McGraw-Hill Book Company (1979) p. 626.
Bell et al., Involvement of NF-kB signalling in skin physiology and disease,Cell Signal.; 15(1):1-7 (2003).
Chun, et al., Nitric oxide induces expression of cyclooxygenase-2 in mouse skin through activation of NF-kB, Carcinogenesis 25:445-454 (2004).
Cosmetic Metallic Powder VISIONAIRE Honey Technical Data Sheet, Mar. 1, 2005, XP55041380.
Data sheet ionto Patch publicly available prior to Jun. 30, 2003.
Davis, Can Acupuncture Punch Up Your Appearance?, Wall Street Journal Health Article, Dec. 21, 2004, p. 107.
Degarmo, et al., Materials and Processes in Manufacturing, 8$^{th}$ Ed., Prentice-Hall, 1997, p. 1096-1110.
Eckart, Internet; "Formulation Guidelines for Formulating Effect Pigments in Water Based Gels", Sep. 1, 2009, pp. 1-5 XP55041406.
Fenton MJ,, Review: Transcriptional and Post-Transcriptional.
Ferry, et al., The Effects of Common Anti-Inflammatory Drugs on the Healing Rat Patellar Tendon, The American Journal of Sports Medicine, vol. 35, No. 8, pp. 1326-1333 (2007).
Flournoy, et al., In Vitro Antimicrobial Susceptibilities of 349 Methicillin-Resistant *Staphylococcus aureus* Isolates from Veterans, Methods Find Exp Clin Pharmacol 12:541-544 (1990).
Fujishima et al., Titanium dioxide photocatalysis, Jun. 29, 2000, Journal of Photochemistry and Photobiology C: Photochemistry Reviews, vol. 1, pp. 1-21.
Garay et al., Journal of the American Academy of Dermatology, vol. 60, Issue 3, Supplement 1, p. AB28 (Mar. 2009).
Goette et al., Skin Blanching Induced by Hydrogen Peroxide, South Med J. 70:620-622 (1977).
Guy, R. H., et al., Arch, Rapid Radial Transport of Methyl Nicotinate in the Dermis,Dermatol Res, 273:91-95 (1982).
Hamamoto et al., Inhibitory effect of azelastine,a potent antiallergic agent, on release of tumor necrosisfactor-CI [raln activated human peripheral blood mononuclear cells and U937 cellsExp Dermatol 2:231-235 (1993).
Hamilton, T.K., Skin Augmentation and Correction: The New Generation of Dermal Fillers—A Dermatologist's Experience, Clinics in Dermatology, 2009:27, S13-S22.
Hunter et al., The Role of Particles in Stabilizing Foams and Emulsion, Mar. 2008, Advances in Colloid and Interface Science, vol. 137, pp. 57-81.
IMWSCC Presentation (SEPPIC, Interest of Rheology and Texture Technology in Cosmetic Research, Nov. 2008, IMWSWCC Presentation, slides 1-54).

(56) References Cited

OTHER PUBLICATIONS

Jacobs, et al., Corrosion of Metal Orthopaedic Implants, The J. of Bone and Joint Surgery (American), 1998, p. 80:268-82.
Jager-Lezer, N., et al., "Rheological Analysis of Highly Concentrated w/o Emulsions", Rheol Acta, vol. 37, pp. 129-138 (1998) XP002685540.
Jumbelic et al., Establishing a Minimal Erythema Concentration of Methyl Nicotinate for Optimum Evaluation of Anti-Inflammatories,Skin Pharmacol Physiol. 19:147-152 (2006).
Kaczmar, J.W., et al., The production and application of metal matrix composite materials, Journal of Materials Processing Technology, vol. 106, Issues 1-3, 2000, p. 58-67.
Kollias et al., In vitro and in vivo Ultraviolet-Induced Alterations of oxy-and Deoxyhemoglobin, Photochem Photobiol. 56:223-227 (1992).
Kruger, Electrochemistry of Corrosion, Electrochemistry Encyclopedia, Apr. 2001, p. 1-10.
Lavoie et al., Light-Induced Byproducts of Vitamin C in Multivitamin Solutions, Clinical Chemistry, 50:1, 135-140 (2004).
Li et al., Ultrafine Zinc and Nickel, Palladium, Silver Coated Zinc Particles Used for Reductive Dehalogenation of Chlorinated Ethylenes in Aqueous Solution, Croatica Chemical Acta CCACAA 71 (4) 853-872 (1998).
Li Y., Biological Properties of Peroxide-containing Tooth Whiteners Food Chem Toxicol., 34:887-904 (1996).
Ligier et al., Formation of the main atmospheric zinc end products] $NaZn_4 Cl(OH)_6 SO_4 ,6H_2O$, $Zn_4SO_4(OH)_6$, $nH_2O$ and $Zn_4Cl_2(OH)_4SO_4 5H_2O$ in [Cl-] {SO24-] [HCO3-} {H2O2] electrolytes, Corrosion Science 41:1139-1164 (1999).
Ly Chan et al., "Treatment of Palmar Hyperhidrosis Using Tap Water Iontophoresis: Local Experience": HKMJ, vol. 5, No. 2, Jun. 1999.
Mastrangelo et al., Exposure to Hydrogen Peroxide and Eye and Nose Symptoms Among Workers in a Beverage Processing Plant, Am. Occup. Hyg. Oxford Univ. Press, pp. 1-5 (2008).
Matula et al., Decontamination of the Oral Cavity. Effect of Six Local Anti-microbial Preparations in Comparison to Water and Parafilm as Controls, J Int Med Res., 16:98-106 (1988).
Miyoshi et al., Age-dependent cell death and the role of ATP in hydrogen peroxide-induced apoptosis and necrosis, PNAS, vol. 103, No. 6, pp. 1727-1731 (Feb. 2006).
Park, H., et al., Effects of electrical stimulation in C2C12 muscle Journal of Tissue Engineering and Regenerative Medicine Research Article.
Procellera™ bioelectric wound dressing, Vomaris Wound Care, Inc., distributed Oct. 22-25, 2009 at 2009 Clinical Symposium on Advances in Skin and Wound Care, San Antonio, TX.
Remington's Pharmaceutical Sciences, Chp. 84, "Emulsions", pp. 1507-1511 (1985).
Sato et al., Generation and transit pathway of H+ is critical for inhibition of palmar sweating by iontophoresis in water, J. Applied Physiology, Nov. 1993; 75: 2258-2264.
Schreiber et al., Adenoviral gene transfer of an NF-kB super-repressor increases collagen deposition in rodent cutaneous wound healing Surgery 138:940-946 (2005).
Sheenan et al., Theory and Practice of Histo-technology (St. Louis: CV Mosby, 1980) pp. 223-277.
Spacciapoli et al., Antimicrobial activity of silver nitrate against periodontal pathogens, Journal of Peridontal Research, 2001, 36:108-113.
Stamatas et al., Blood stasis contributions to the perception of skin pigmentation, Journal Biomedical Optics 9(2), pp. 315-322 (Mar./Apr. 2004).
Stux et al., Basics of Acupuncture, Springer 2003 pp. 306-309.
Sun et al., Intestinal Electric Stimulation Decreases Fat Absorption in Rats: Therapeutic Potential for Obesity, Obesity Research, vol. 12, No. 8, Aug. 2004, p. 1235-1242.
Sur et al., Anti-Inflammatory Activity of Sertaconazole Nitrate Is Mediated via Activation of a p38—COX-2-PGE2 Pathway J Invest Dermatol. 128(2):336-344 (2008).
T. Johnson, CRC Ethnobotany Desk Reference, 1998 Ed, p. 198-199.
T. Johnson, CRC Ethnobotany Desk Reference, 1998 Ed, p. 516-517.
T. Johnson, CRC Ethnobotany Desk Reference, 1998 Ed, p. 823-824.
Yang et al., Use of caryophyllene oxide as an antifungal agent in an in vitro experimental model of onychomycosis, *Mycopathologia* 148:79-82 (1999).
Zhang, Corrosion and Electrochemistry of Zinc, 1996, p. 217-236.
Eming, S.A. et. al. 'Inflammation in Wound Repair: Molecular and Cellular Mechanisms' Journal of Investigative Dermatology (2007) vol. 127 pp. 514-525.
Sebastian, A. et. al., Acceleration of cutaneous healing by electrical stimulation: Degenerate electrical waveform down-regulates inflammation, up-regulates angiogenesis and advances remodeling in temporal punch biopsies in a human volunteer study Wound Repair and Regeneration (2011) vol. 19 pp. 693-7108.
Janotti, A. et al., "Fundamentals of Zinc Oxide as a Semiconductor," Reports on Progress in Physics, 72 (2009), 126510, pp. 1-29.
Michels et al. Copper Alloys for Human Infectious Disease Control, Presented at Materials Science and Technology Conference, Sep. 25-28, 2005, Pittsburgh, PA, Copper for the 21st Century Symposium, pp. 1-11.
Zhu Zhenguo Ed, Practical Physiotherapy, Published and Issued by Nanjing Publishing House, Jan. 1997, 3 pages.
"Brass" by Collins English Dictionary, http://www.xreferplus.com/entry/hcengdict/brass, accessed Sep. 18, 2012.
Cosmetic Metallic Powder VISIONAIRE Natural Gold Technical Data Sheet, Mar. 1, 2005, XP55041380.
Zhao et al., Canadian Journal of Microbiology, 44:441-7 (1998) (Abstract Only (Pubmed)).
Library of Congress Cataloging-in-Publication Data, Electroanalytical Methods, Table 14.1, McGraw Hill Inc. 1995 pp. 14-3-14.16.
Fenton MJ,, Review: Transcriptional and Post-Transcriptional Regulation of Interleukin 1 Gene Expression, 1992, vol. 14, No. 3, pp. 401-441.
Park, H., et al., Effects of electrical stimulation in C2C12 muscle constructs, Journal of Tissue Engineering and Regenerative Medicine, 2008, pp. 279-287.
*Helicobacter pylori*, CDC Fact Sheet for Health Care Providers (1998).
Na et al. "Control of palmar hyperhidrosis with a nee "dry-type" iontophoretic device", Dermatologic Surgery, vol. 33, No. 1' Jan. 1, 2007, pp. 57-61, XP055130862, ISSN: 1076-0512, DOI: 10.1111/j.1524-4725.2007.33007.x, Abstract.
Lim et al. Topical botulinum toxin to treat hyperhidrosis? No sweat!, Medical Hypotheses, Eden Press, Penrith, US, vol. 67, No. 1, Jan. 1, 2006, pp. 27-32, XP005397008, ISSN: 0306-9877, DOI: 10.1016/J.MEHGY.2006.01.012 Table.
Shelley et al. "Experimental miliaria in man. IV. Sweat retention vesicles following destruction of terminal sweat duct", The Journal of Investigative Dermatology, vol. 16, No. 1, Jan. 1, 1951, pp. 53-64, XP055129416, GB ISSN: 0022-202X, DOI: 10.1 038/jid.1951. 7, p. 54, paragraph 4.

\* cited by examiner

US 9,044,397 B2

MEDICAL DEVICES WITH GALVANIC PARTICULATES

CROSS REFERENCE TO RELATED APPLICATIONS

This application is a divisional application of U.S. application Ser. No. 13/207,398, filed Aug. 10, 2011 which is a continuation-in-part of U.S. application Ser. No. 12/890,881, filed on Sep. 27, 2010 which is a continuation-in-part of U.S. application Ser. No. 12/761,601, filed on Apr. 16, 2010, which is a continuation in part of nonprovisional U.S. application Ser. No. 12/731,848 filed on Mar. 25, 2010, which claims priority to the provisional U.S. Application Ser. No. 61/163,928, filed Mar. 27, 2009, which is incorporated herein by reference.

FIELD OF THE INVENTION

This invention relates to antimicrobial medical devices, more specifically antimicrobial devices containing or coated with galvanic particulates.

BACKGROUND OF THE INVENTION

Medical devices are typically sterilized prior to use. Most medical devices are packaged in packaging which maintains the sterility of the device until the package is opened by the health care provider at the site where the health care services are being administered or provided. Depending upon the environment in which the devices are used, it is possible for the device to be contaminated with microbes prior to use or during insertion, or after insertion or implantation if the implantation site in the patient is contaminated, for example as a result of trauma or faulty or inadequate sterile procedures. Microbial contamination of medical devices can result in serious infections in the patient which are often not easily treatable for a variety of reasons, including the formation of antibiotic resistant biofilms. The use of antimicrobial coatings on medical devices may eliminate or diminish the incidence of infections associated with the use or implantation of medical devices. In addition to bacterial contamination and tissue infection, many postsurgical complications are caused by excess tissue inflammation, leading to pain and edema at the surgical or implant site, scarring and tissue adhesion.

Using a galvanic couple as the power source in iontophoresis patch devices is known in the art. See, for example, U.S. Pat. Nos. 5,147,297, 5,162,043, 5,298,017, 5,326,341, 5,405,317, 5,685,837, 6,584,349, 6,421,561, 6,653,014, and U.S. Patent Application US 2004/0138712. The galvanic couple is made from powders of dissimilar metals, such as a zinc donor electrode and a silver chloride counter electrode. Some of these galvanic couple powered topical iontophoresis patch devices activate automatically when body tissue and/or fluids form a complete circuit with the galvanic system to generate the electricity. These devices are applied to the human body in order to provide an intended benefit, such as electrical stimulation, enhanced wound healing, or antimicrobial treatment. Other types of topical systems powered by galvanic couples its the form of particulates are disclosed in U.S. Pat. Nos. 7,476,221, 7,479,133, 7,477,939, 7,476,222, 7,477,940, and U.S. Patent Applications US 2005/0148996 and US 2007/0060862, which have, inter alia, disclosures directed toward topical treatments of skin and mucosal tissues.

The aforementioned galvanic treatment systems have been recognized as being useful in topical therapeutic products for the skin, nails, hair and mucosal conditions and diseases. There is a need in this art for novel implantable medical devices that have enhanced antimicrobial properties while retaining the biocompatible nature and mechanical functionality of the device, and which may have additional advantages such as anti-inflammatory and tissue regenerative properties.

SUMMARY OF THE INVENTION

Implantable medical devices having antimicrobial, properties are disclosed. The medical devices contain galvanic particulates. The galvanic particulates may be present on the surface of the device, in the hulk of the device, or combinations thereof. Another aspect of the present invention is a medical device coated on at least one part of a surface with an antimicrobial coating that contains galvanic particulates. Medical devices having galvanic particulates are useful for preventing, reducing or eliminating infection at the implant site. The devices may also have other beneficial properties including anti-inflammatory and tissue regenerative properties.

Yet another aspect of the present invention is a method of manufacturing the above-described medical devices.

Still yet another aspect of the present invention is a method of using the above-described devices in a surgical procedure.

Another aspect of the present invention is a combination of galvanic particulates with an aqueous gel. A further aspect of the present invention is a method of manufacturing the combination of galvanic particulates with an aqueous gel as well as a method of treatment using said combination.

These and other aspects and advantages of the present invention will become more apparent from the following description and accompanying drawings.

DETAILED DESCRIPTION OF THE INVENTION

Figure 1:
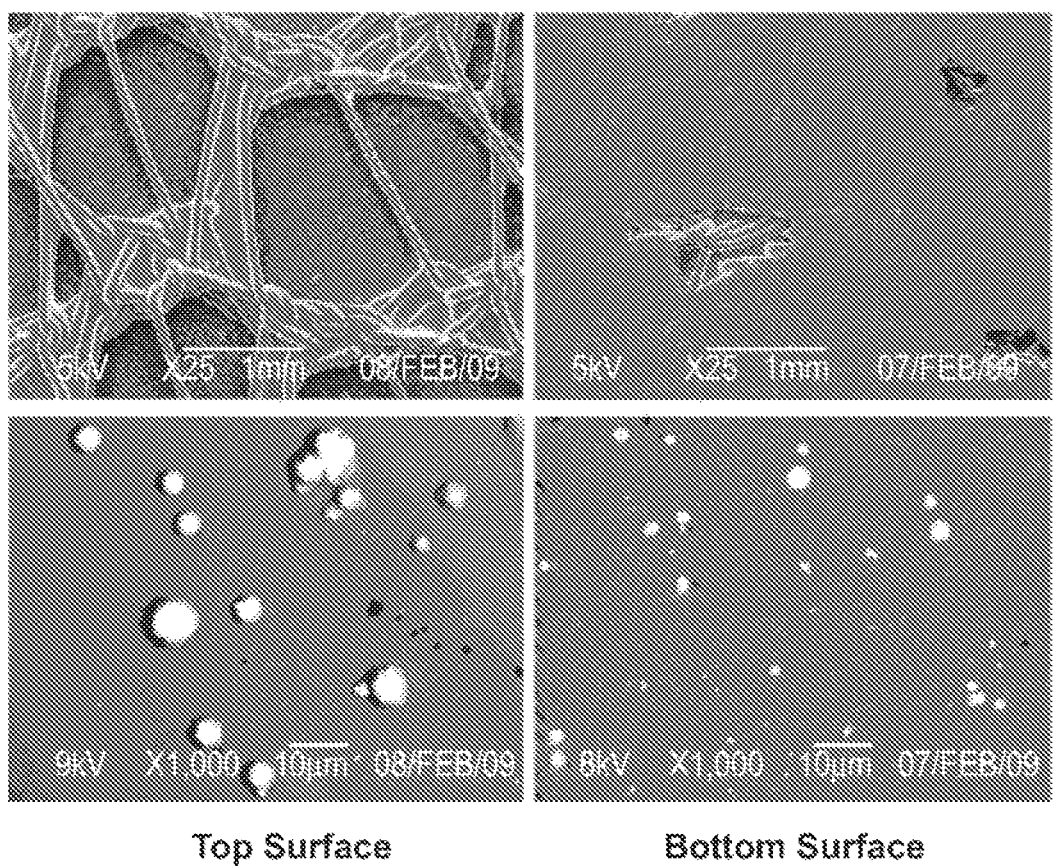
FIG. 1 is a SEM Image of polypropylene mesh coated with Zn/Cu galvanic particulates using a hot attachment process.

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, a percentage refers to a percentage by weight (i.e., % (W/W)).

As used herein, "product" means a medical device of the present invention coated with a coating containing galvanic particles or having galvanic particulates embedded or contained therein.

As used herein, "pharmaceutically-acceptable" means that the ingredients which the term describes are suitable for their intended medical use without undue toxicity, incompatibility, instability, irritation, allergic response, and the like.

As used herein, "safe and effective amount" means an amount of the ingredient or the composition sufficient to provide the desired benefit at a desired level, but low enough to avoid serious side effects. The safe and effective amount of the ingredient or composition will vary with conventional factors including the area being treated, the age and individual characteristics of the patient, the duration and nature of the treatment, the specific ingredient or composition employed, the particular pharmaceutically-acceptable carrier utilized, and like factors.

As used herein, the term "treating" or "treatment" means the treatment (e.g., alleviation or elimination of symptoms and/or cure) and/or prevention or inhibition of the conditions (e.g., infection, inflammation, pain, edema and/or other post-surgical and post-procedural complications). The procedures include open surgery and medical procedures (e.g., injection, inserting catheters) and minimally invasive procedures. A minimally invasive procedure is any procedure (surgical or otherwise) that is less invasive than open surgery used for the same purpose. A minimally invasive procedure typically involves the use of laparoscopic and remote-control manipulation of instruments with indirect observation of the surgical field through an endoscope similar device, and are carried out through the skin or through a body cavity or anatomical opening.

The terms particulate and particulates are used interchangeably herein. The terms particles is used interchangeably with the terms particulate and particulates.

In one embodiment, the invention, as described herein, is a medical device comprising a galvanic particulate. The galvanic particulate may be incorporated onto the surface of the device, into the bulk of the medical device, and combinations thereof. Methods of making such a medical device are also described.

The galvanic particulates useful in the present invention include a first conductive material and a second conductive material, wherein both the first conductive material and the second conductive material are at least partially exposed on the surface of the particulate. In one embodiment, the particulate includes the first conductive material and the surface of the particulate is partially coated with the second conductive material.

In one embodiment, the galvanic particulates are produced by a coating method wherein the weight percentage of the second conductive material is from about 0.001% to about 20%, by weight, of the total weight of the particulate, such as from about 0.01% to about 10%, by weight, of the total weight of the particulate. In one embodiment, the coating thickness of the second conductive material may vary from single atom up to hundreds of microns. In yet another embodiment, the surface of the galvanic particulate comprises from about 0.001 wt. % to about 99.99 wt. % such as from about 0.1 wt. % to about 99.9 wt. % percent of the second conductive material.

In one embodiment, the galvanic particulates are produced by a non-coating method (e.g., by sintering, printing or mechanical processing the first and the second conductive materials together to form the galvanic particulate) wherein the second conductive material comprises from about 0.1% to about 99.9%, by weight, of the total weight of the particulate, and other ranges for example from about 10% to about 90%, of the total weight of the particulate.

In one embodiment, the galvanic particulates are fine enough that they can be suspended in the compositions during storage. In a further embodiment, they are in flattened and/or elongated shapes. The advantages of flattened and elongated shapes of the galvanic particulates include a lower apparent density and, therefore, a better floating/suspending capability, as well as better coverage over biological tissue, leading to a wider and/or deeper range of the galvanic current passing through the biological tissue (e.g., the skin or mucosa membrane). In one embodiment, the longest dimension of the galvanic particulates is at least twice (e.g., at least five times) the shortest dimension of such particulates. In another embodiment, the shape of the galvanic particulate is a thin flake, with its thickness (Z-axis) significantly smaller than its other two dimensions (X and Y dimensions), for example, with its thickness from about 0.5 to 1.5 micrometers and its other two dimensions ranging from about 5 micrometers to about 100 micrometers.

The galvanic particulates may be of any shape, including but not limited to, spherical or non-spherical particles or elongated or flattened shapes (e.g., cylindrical, fibers or flakes). In one embodiment, the average particle size of the galvanic particulates is from about 10 nanometers to about 500 micrometers, such as from about 100 nanometers to about 100 micrometers. What is meant by the particle size is the maximum dimension in at least one direction. Optionally, the galvanic particulates may be sieved to obtain the desired particle size range. Sieving galvanic particulates may be advantageous in providing a narrow size distribution of particles or to remove fines or agglomerates, which may be particularly useful in injectable formulations described below.

Examples of combinations of first conductive materials/ second conductive materials are elemental metals that include (with a "/" sign representing an oxidized but essentially non-soluble form of the metal), but are not limited to, zinc-copper, zinc-copper/copper halide, zinc-copper/copper oxide, magnesium-copper, magnesium-copper/copper halide, zinc-silver, zinc-silver/silver oxide, zinc-silver/silver halide, zinc-silver/silver chloride, zinc-silver/silver bromide, zinc-silver/silver iodide, zinc-silver/silver fluoride, zinc-gold, zinc-carbon, magnesium-gold, magnesium-silver, magnesium-silver/silver oxide, magnesium-silver/silver halide, magnesium-silver/silver chloride, magnesium-silver/silver bromide, magnesium-silver/silver iodide, magnesium-silver/silver fluoride, magnesium-carbon, aluminum-copper, aluminum-gold, aluminum-silver, aluminum-silver/silver oxide, aluminum-silver/silver halide, aluminum-silver/silver chloride, aluminum-silver/silver bromide, aluminum-silver/silver iodide, aluminum-silver/silver fluoride, aluminum-carbon, copper-silver/silver halide, copper-silver/silver chloride, copper-silver/silver bromide, copper-silver/silver iodide, copper-silver/silver fluoride, iron-copper, iron-copper/copper oxide, copper-carbon iron-copper/copper halide, iron-silver, iron-silver/silver oxide, iron-silver/silver halide, iron-silver/silver chloride, iron-silver/silver bromide, iron-silver/silver iodide, iron-silver/silver fluoride, iron-gold, iron-conductive carbon, zinc-conductive carbon, copper-conductive carbon, magnesium-conductive carbon, and aluminum-carbon.

The first conductive material or second conductive material may also be alloys, particularly the first conductive material. Non-limiting examples of the alloys include alloys of zinc, iron, aluminum, magnesium, copper and manganese as the first conductive material and alloys of silver, copper, stainless steel and gold as second conductive material.

In one embodiment, the particulate, made of the first conductive material, is partially coated with several conductive materials, such as with a second and third conductive material. In a further embodiment, the particulate comprises at least 95 percent by weight of the first conductive material, the second conductive material, and the third conductive material. In one embodiment, the first conductive material is zinc, the second conductive material is copper, and the third conductive material is silver. Standard electrode potential is potential of an electrode composed of a substance in its standard state, in equilibrium with ions in their standard states compared to a hydrogen electrode. In one embodiment, the difference of the standard electrode potentials (or simply, standard potential) of the first conductive material and the second conductive material is at least about 0.1 volts, such as at least 0.2 volts. In one embodiment, the materials that make up the galvanic couple have a standard potential difference equal to or less than about 3 volts. For example, for a galvanic couple comprised of metallic zinc and copper, the standard potential of zinc is $-0.763$ V ($Zn/Zn2^+$), and the standard potential of copper is $+0.337$ ($Cu/Cu2^+$), the difference of the standard potential is therefore 1.100 V for the zinc-copper galvanic couple. Similarly, for the magnesium-copper galvanic couple, standard potential of magnesium ($Mg/Mg2^+$) is $-2.363$V, and the difference of the standard potential is therefore 2.700V. Additional examples of standard potential values of some materials suitable for galvanic couples are: $Ag/Ag^+$: $+0.799$V, $Ag/AgCl/Cl^-$:$0.222$V, and $Pt/H_2/H^+$:$0.000$V. Pt may also be replaced by carbon or another conductive material. In general, the voltage between the conductive materials will be sufficient to effectively provide a desired therapeutic effect.

In one embodiment, the conductive electrodes are combined (e.g., the second conductive electrode is deposited to the first conductive electrode) by conventional chemical, electrochemical, physical or mechanical process (such as electroless deposition, electric plating, vacuum vapor deposition, arc spray, sintering, compacting, pressing, extrusion, printing, and granulation) conductive metal ink (e.g., with polymeric binders), and other known metal coating and powder processing methods commonly used in powder metallurgy, electronics and medical device manufacturing processes. In another embodiment, all of the conductive electrodes are manufactured by conventional chemical reduction processes (e.g., electroless deposition), sequentially or simultaneously, in the presence of reducing agent(s). Examples of reducing agents include phosphorous-containing reducing agents (e.g., a hypophosphite as described in U.S. Pat. Nos. 4,167,416 and 5,304,403), boron-containing reducing agents, and aldehyde- or ketone-containing reducing agents such as sodium tetrahydroborate (NaBH4) (e.g., as described in US Patent Publication No. 20050175649).

In one embodiment, the second conductive electrode is deposited or coated onto the first conductive electrode by physical deposition, such as spray coating, plasma coating, conductive ink coating, screen printing, dip coating, metals bonding, bombarding particulates under high pressure-high temperature, fluid bed processing, or vacuum deposition.

In one embodiment, the coating method is based on a displacement chemical reaction, namely, contacting a particulate of the first conductive material (e.g., metallic zinc particle) with a solution containing a dissolved salt of the second conductive material (e.g., copper acetate, copper lactate, copper gluconate, or silver nitrate). In a further embodiment, the method includes flowing the solution over the particulate of the first conductive material (e.g., zinc powder) or through the packed powder of the first conductive material. In one embodiment, the salt solution is an aqueous solution. In another embodiment, the solution contains an organic solvent, such as an alcohol, a glycol, glycerin or other commonly used solvents in pharmaceutical production to regulate the deposition rate of the second conductive material onto the surfaces of the first particulates, therefore controlling the activity of the galvanic particulates produced.

In another embodiment, the galvanic particulates of the present invention may also be coated with other materials to protect the galvanic materials from degradation during storage (e.g., oxidation degradation from oxygen and moisture), or to modulate the electrochemical reactions and to control the electric current generate when in use. The exemplary coating materials over the galvanic material(s) are inorganic or organic polymers, natural or synthetic polymers, biodegradable or bioabsorbable polymers, silica, ceramic, various metal oxides (e.g., oxide of zinc, aluminum, magnesium, or titanium (and other inorganic salts of low solubility (e.g., zinc phosphate). The coating methods are known in the art of metallic powder processing and metal pigment productions, such as those described by U.S. Pat. No. 5,964,936, U.S. Pat. No. 5,993,526, U.S. Pat. No. 7,172,812; U.S. Patent Publication Nos. 20060042509A1 and 20070172438.

In one embodiment, the galvanic particulates are stored in a dry, nitrogen environment. The galvanic particulates are activated by moisture to provide a galvanic battery. It is preferred that they be kept is a moisture free environment to prevent premature activation of the particles. In another embodiment, the galvanic particulates are stored in a nonconductive vehicle, such as an anhydrous solvent or a solvent mixture, which includes, but is not limited to, polyethylene glycol (PEG), glycerin, and propylene glycol.

In one embodiment, the galvanic particulates are incorporated into or onto medical devices and implants. Suitable medical devices that may contain or be coated with the galvanic particles include, but are not limited to, wound closure staples, sutures, suture anchors, surgical needles, hypodermic needles, catheters, wound tape, wound dressing, hemostats, stents, vascular grubs, vascular patches, catheters, surgical meshes, bone implants, joint implants, prosthetic implants, bone grafts, dental implants, breast implants, tissue augmentation, implants, plastic reconstruction implants, implantable drug delivery pumps, diagnostic implants and tissue engineering scaffolds and other conventional medical devices and equivalents thereof. The medical devices may be prepared or made from conventional biocompatible absorbable or resorbable polymers, nonabsorbable polymers, metals, glasses or ceramics and equivalents thereof.

Suitable nonabsorbable polymers include, but are not limited to acrylics, polyamide-imide (PAI), polyacryletherketones (PEEK), polycarbonate, polyethylenes (PE), polybutylene terephthalates (PBT) and polyethylene (PET), terephthalates, polypropylene, polyamide (PA), polyvinylidene fluoride (PVDF), and polyvinylidene fluoride, -co-hexafluoropropylene (PVDF/HFP), polymethylmetacrylate (PMMA) and combinations thereof and equivalents.

Suitable absorbable polymers may be synthetic or natural polymers. Suitable biocompatible, bioabsorbable polymers include polymers selected from the group consisting of aliphatic polyesters, poly (amino acids), copoly (ether-esters), polyalkylenes, oxalates, polyamides, tyrosine derived polycarbonates, poly (iminocarbonates), polyorthoesters, polyoxaesters, polyamidoesters, polyoxaesters containing amine groups, poly (anhydrides), polyphosphazenes, and combinations thereof. For the purpose of this invention aliphatic polyesters include, but are not limited to, homopolymers and copolymers of lactide (which includes lactic acid, D-, L- and meso lactide), glycolide (including glycolic acid), epsilon-caprolactone, p-dioxanone (1,4-dioxan-2-one), trimethylene carbonate (1,3-dioxan-2-one), alkyl derivatives of trimethylene carbonate, and polymer blends thereof. Natural polymers include collagen, elastin, hyaluronic acid, laminin, and gelatin, keratin, chondroitin sulfate and decellularized tissue.

Suitable metals are those biocompatible metals used conventionally in medical devices including, but not limited to titanium, titanium, alloys, tantalum, tantalum alloys, stainless steel, and cobalt-chromium alloys (e.g., cobalt-chromium-molybdenum alloy) and the like. These metals are conventionally used in sutures, surgical needles, orthopedic implants, wound staples, vascular staples, heart valves, plastic surgery implants, other implantable devices and the like.

Suitable absorbable or biocompatible glasses or ceramics include, but are not limited to phosphates such as hydroxyapatite, substituted apatites, tetracalcium phosphate, alpha- and beta-tricalcium phosphate, octacalcium phosphate, brushite, monetite, metaphosphates, pyrophosphates, phosphate glasses, carbonates, sulfates and oxides of calcium and magnesium, and combinations thereof.

In the practice of the present invention, galvanic particulates may be combined with medical devices by various methods including coating the galvanic particulate on at least part of a surface of the medical device, incorporating the galvanic particulate into the medical device, and combinations thereof. Incorporating the galvanic particulate into the medical device allows for a sustained activity of the particles which are exposed over time as in the case of absorbable polymers. The galvanic particles are activated by moisture; therefore all processing of the particles should be carried out under dry or substantially dry conditions.

Galvanic particulate may be coated on the surface of the medical device by directly attaching the particles to the device or by using a polymeric binder, including conventional biocompatible polymeric binders. The particles may also be directly attached to the device by heating the particles. The particles may be attached to the surface of a medical device prepared from polymers or devices having a polymer coating as a binder by heating the particles to a temperature sufficient to melt the surface of the medical device, followed by impacting the particle with the device surface, which temporarily melts or softens the surface and then cools allowing the particle to be placed on or embedded in or otherwise adhered to the surface of the device. The heated particles may be applied by conventional coating methods such as electrostatic spraying, fluidized bed coating, and the like. Alternatively, a polymeric film can be coated on the surface of a device, and this film is then heated and the particulate is applied to the softened film as described above.

Alternatively a polymer binder coating may be used to apply or attach the particles to the medical devices. The galvanic particles may be combined with a solution containing the polymer binder. Suitable polymer binders include those used to prepare medical devices listed above. Suitable solvents include 1,4-dioxane, ethyl acetate and the like. One of skill in the art can determine the appropriate solvent based upon the polymer composition. The polymer binder is dissolved in a suitable solvent in the concentration of about 1 weight % to about 15 weight %. The galvanic particles may be present in the polymer binder solution in the amount of about 7.5 weight % to about 10 weight %. The coatings containing the galvanic particles in the polymer binder solution may be used to coat the medical devices, typically all or part of outer surfaces although inner surfaces may be coated as well, by conventional methods such as microspray coating, electrostatic spraying, electrostatic spinning, dip coating, fluidized bed coating and the like.

The amount of galvanic particles on the coated surface of a medical device will be sufficient to effectively elicit antimicrobial and/or anti-inflammatory and/or anti-adhesion actions in a safe and efficacious manner. In one embodiment, the galvanic particles may be present on the surface of the device in the amount of about 0.001 mg/in$^2$ to about 20 mg/in$^2$. In another embodiment the galvanic particles may be present on the surface of the device in the amount of about 0.1 mg/hr to 10 mg/in$^2$.

Galvanic particulate may also be incorporated into the medical device by conventional methods such as compounding, solvent casting, lyophilization, electrostatic spinning, extrusion, and the like.

The particles may be compounded into a composite with molten polymers in a static mixer or continuous extruder. The composite of the particles and polymer can be further processed into devices using methods including extrusion, injection molding, compression molding, and other melting processes. Suitable polymers include those used to prepare medical devices listed above. In one embodiment, the particulate loading is the composite may be about 0.001 weight % to about 80% by weight. In another embodiment the particulate loading in the composite may be about 0.01 weight % to about 20 weight %. One of skill in the art can determine suitable processing conditions for the desired polymer composition.

Alternatively, a polymer solution may be used to incorporate the galvanic particulates into the medical devices by methods such as solvent casting, lyophilization, electrostatic spinning and the like. The galvanic particles may be combined with a polymer solution. Suitable polymers include those used to prepare medical devices listed above. Suitable solvents include 1,4-dioxane, ethyl, acetate and the like. One of skill in the art can determine the appropriate solvent based upon the polymer composition. The polymer is dissolved in a suitable solvent in the concentration of about 1 weight % to about 15 weight %. The galvanic particles may be present in the polymer solution in the amount of about 7.5 weight % to about 10 weight %. Such galvanic particulate/polymer solutions may be used in conventional processes including solvent casting to provide films, lyophilization to provide foam medical devices, and electrostatic spinning to prepare fibers, tubes, mats and the like.

Galvanic particulates may also be combined with an aqueous composition, such as aqueous gel or emulsion. The particulates may be mixed with an aqueous gel at the point of use. The galvanic particles may be present in the aqueous gel in the amount of about 0.0001 weight % to about 10 weight %, and preferably about 0.001 weight % to about 1 weight %. In another embodiment, a mixture of galvanic particulates and suitable polymers in a dry form may be hydrated at the point of use. The suitable polymers include, but are not limited to carboxyl methylcellulose (CMC), hyaluronic acid (HA), PEG, alginate, chitosan, chondroitin sulfate, dextran sulfate, and polymer blend and their salts thereof. Suitable aqueous solvents are water, physiological saline, phosphate-buffered saline, and the like.

In one aspect, formulations or compositions are disclosed for treating a joint condition comprising a formulation. The formulation or composition can be in liquid form. The liquid formulation can also be stable at room temperature. Moreover, the liquid formulation can include a solution of hyaluronic acid (HA). The HA formulation can be a high molecular weight HA. The molecular weight can be, for example, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000 kDa or more, or any range derivable therein. In exemplary embodiments, the HA has a molecular weight in the range of about 1 MDa to 6 MDa. In another exemplary embodiment, the HA has a molecular weight greater than 1 MDa.

Moreover, the HA formulation can be present at particular concentrations. In one embodiment, the HA is present at a concentration of at least about 7 mg/ml. In another exemplary embodiment, the HA has a concentration of at least about 5 mg/ml, and more preferably at least about 7 mg/ml, and more preferably at least about 10 mg/ml, and more preferably at least about 15 mg/ml, and in some embodiments the concentration can be at least about 25 mg/ml. In another embodiment, the HA can have a concentration in the range of about 1.5 mg/ml to about 25 mg/ml.

In another aspect, the formulation or composition includes at least one additional component. The additional component added to the formulation or composition can be, for example, amino acids, amino sugars, sugar alcohols, proteins, saccharides, di-saccharides, oligo-saccharides, poly-saccharides, nucleic acids, buffers, surfactants, lipids, liposomes, other excipients, and mixtures thereof. Other useful components can include steroids, anti-inflammatory agents, non-steroidal anti-inflammatory agents, analgesics, cells, antibiotics, antimicrobial agents, anti-inflammatory agents, growth factors, growth factor fragments, small-molecule wound healing stimulants, hormones, cytokines, peptides, antibodies, enzymes, isolated cells, platelets, immunosuppressants, nucleic acids, cell types, viruses, virus particles, essential nutrients, minerals, metals, or vitamins, and combinations thereof. Additionally, the formulation or composition can include a diluent, such as water, saline, or a buffer.

Hyaluronic add (HA) can have various formulations and can be provided at various concentrations and molecular weights. The terms "hyaluronic acid," "hyaluronan," "hyaluronate," and "HA" are used interchangeably herein to refer to hyaluronic acids or salts of hyaluronic acid, such as the sodium, potassium, magnesium, and calcium salts, among others. These terms are also intended to include not only pure hyaluronic acid solutions, but hyaluronic acid, with other trace elements or in various compositions with other elements. The terms "hyaluronic acid," "hyaluronan," and "HA" encompass chemical or polymeric or cross-linked derivatives of HA. Examples of chemical modifications which may be made to HA include any reaction of an agent with the four reactive groups of HA, namely the acetamido, carboxyl, hydroxyl, and the reducing end. The HA used in the present application is intended to include natural formulations (isolated from animal tissue) or synthetic formulations (derived from bacterial fermentation) or combinations thereof. The HA can be provided in liquid form or solid formulations that is reconstituted with a diluents to achieve an appropriate concentration.

The methods of treatment can include directly injecting the compositions into the target area, such as a joint. Injections can be performed as often as daily, weekly, several times a week, bi monthly, several times a month, monthly, or as often as needed as to provide relief of symptoms. For intra-articular use, from about 1 to about 30 mg/ml of HA per joint, depending on the size of the joint and severity of the condition, can be injected. The frequency of subsequent injections into a given joint are spaced to the time of recurrence of symptoms in the joint. Illustratively, dosage levels in humans of the composition can be: knee, about 1 to about 30 mg/ml per joint injection; shoulder, about 1 to about 30 mg/ml of HA per joint injection; metacarpal or proximal intraphalangeal, about 1 mg/ml to about 30 mg/ml of HA per joint injection; and elbow, about 1 to about 30 mg/ml per joint inflection. The total amount of injection can range from about 1 mg/ml to 200 mg/ml of HA.

It will be understood, however, that the specific dosage level for any particular patient will depend upon a variety of factors including the activity of the specific compound employed, the age, body weight, general health, sex, diet, time of administration, route of administration, rate of excretion, drug combination and the severity of the particular disease undergoing therapy. The pharmaceutical compositions can be prepared and administered in dose units. Under certain circumstances, however, higher or lower dose units may be appropriate. The administration of the dose unit can be carried out both by single administration of the composition or administration can be performed in several smaller dose units and also by multiple administrations of subdivided doses at specific intervals.

In one embodiment, the medical condition is osteoarthritis (OA) and the composition is administered in a joint space, such as, for example, a knee, shoulder, temporo-mandibular and carpo-metacarpal joints, elbow, hip, wrist, ankle, and lumbar zygapophysial (facet) joints in the spine. The viscosupplementation may be accomplished via a single injection or multiple intraarticular injections administered over a period of weeks into the knee or other afflicted joints. For example, a human subject with knee OA may receive one, two, three, four, or five injections of about 0.5, 1, 1.5, 2, 3, 4, 5, 6, 7, 8, 9, 10 ml or more per knee. For other joints, the administered volume can be adjusted based on the size on the joint.

It will be understood, however, that the specific dosage level for any particular patient will depend upon a variety of factors including the activity of the specific compound employed, the age, body weight, general health, sex, diet, time of administration, route of administration, rate of excretion, drug combination and the severity of the particular disease undergoing therapy.

Medical devices of the present invention comprising galvanic particulates are useful for preventing, reducing, or eliminating infection at the implant site. It will be appreciated that such devices will be used with other aspects of infection control including sterile procedures, antibiotic administration, etc. For example, mesh coated with galvanic particles (or otherwise containing galvanic particles) can be used for contaminated hernia repair or contaminated trauma repair with significantly reduced concerns about the generation of antibiotic resistant bacteria including biofilms. Alternatively, an anti-infective hemostat containing galvanic particles can be useful for traumatic and post-surgical bleeding control. The medical devices of the present invention having galvanic particulates can be used in addition to conventional methods for infection control, such as oral or IV administration of antibiotics to enhance the efficacy of the conventional treatment methods for infection control. Incorporation in and coating of medical devices with galvanic particles can improve the biocompatibility of the devices and enhance tissue-device integration and promote wound repair by suppressing inflammatory reaction.

In one embodiment, the medical devices with galvanic particulates are used to provide the intended therapeutic galvanic electric stimulation effects to promote tissue regeneration, repair and growth by applying the galvanic particulates directly to the target location of the body in need such a therapeutic treatment (e.g., either topically or inside the body), including soft tissues (e.g., the skin, mucosa, epithelium, wound, eye and its surrounding tissues, cartilage and other soft musculoskeletal tissues such as ligaments, tendons, or meniscus), hard tissues (e.g., bone, teeth, nail matrix, or hair follicle), and soft tissue-hard tissue conjunctions (e.g., conductive tissues around periodontal area involved teeth, bones or soft tissue of the joint). In one embodiment, the galvanic particulate medical device is administered alone. In another embodiment, additional galvanic particulates are administered locally with the galvanic particulate medical device to the subject (e.g., a human) in need of such treatment via a surgical procedure or a minimally invasive procedure.

Such therapeutic effects include, but are not limited to: antimicrobial effects (e.g., antibacterial, antifungal, antiviral, and anti-parasitic effects); anti-inflammation effects including effects in the superficial or deep tissues (e.g., reduce or elimination of soft tissue edema or redness); prevention of post-surgical tissue adhesion (anti-adhesion); elimination or reduction of pain, itch or other sensory discomfort (e.g., headache, sting or tingling numbness); regeneration or healing enhancement of both soft and hard tissues; modulation of stem cell differentiation and tissue development such as modulation of tissue growth (e.g., enhancing growth rate of the nail or regrowth of hair loss due to alopecia) or increase soft tissue volume (e.g., increasing collagen or elastin in the skin or lips); increasing adipocyte metabolism or improving body appearance (e.g., effects on body contour or shape); and increasing circulation of blood or lymphocytes.

In one embodiment, the medical devices with galvanic particulates provide multiple mechanisms of actions to treat conditions, such as to enhance delivery of an active agents by iontophoresis and/or electro-osmosis as well as provide electric stimulation to treat the contacted tissue (e.g., to increase blood circulation or other benefits). What is meant by an "active agent" is a compound (e.g., a synthetic compound, a compound isolated from a natural source or manufactured through bioengineering and molecular biology methods) that has a therapeutic effect on the target human tissue or organ and the surrounding tissues (e.g., a material capable of exerting a biological effect on a human body) such as therapeutic drugs or biological agents. Examples of such therapeutic drugs include small molecules, peptides, proteins, nucleic acid materials, and nutrients such as minerals and extracts. The amount of the active agent in the carrier will depend on the active agent and/or the intended use of the composition or product. In one embodiment, the medical device having the galvanic particulates further contain a safe and therapeutically effective amount of the active agent, for example, from about 0.001 percent to about 20 percent, by weight, such as from about 0.01 percent to about 10 percent, by weight, of the composition.

In one embodiment, the medical devices with galvanic particulates can be combined with an active agent (such as antimicrobial agents, anti-inflammatory agents, analgesic agents, and biological agents) to be incorporated into a medical device (e.g., as a surface coating or embedded within) to enhance or potentiate the biological or therapeutic effects of that active agent. In another embodiment, the galvanic particulates can be incorporated into a medical device to work efficacious or synergistically with one or more than one active agent administered by a different route of administration concurrently or sequentially (e.g., by systemic route such as oral dosing, injection or infusion) to enhance or potentiate the biological or therapeutic effects of that active agent. For example, a medical implant with a galvanic particulate coating can be applied to a patient through a surgical procedure, whereas a systemic antibiotic therapy can be administered either prior to or shortly alter the procedure as prophylaxsis to prevent or treat any post-surgical infections. In yet another embodiment, the galvanic particulates can also be combined with other substances to enhance or potentiate the activity of the galvanic particulates. Substances that can enhance or potentiate the activity of the galvanic particulates include, but are not limited to, organic solvents, surfactants, and water-soluble polymers. For example, the galvanic particulates of the present invention can form conjugates or composites with synthetic or natural polymers including by not limited to proteins, polysaccharides, hyaluronic acid of various molecular weight, hyaluronic acid analogs, polypeptides, and collagens of different origins.

In one embodiment, the composition contains a chelator or chelating agent. Examples of chelators include, but are not limited to, amino acids such as glycine, lactoferrin, edetate, citrate, pentetate, tromethamine, sorbate, ascorbate, deferoxamine, derivatives thereof, and mixtures thereof. Other examples of chelators useful are disclosed in U.S. Pat. No. 5,487,884 and PCT Publication No. WO2006056984. In one embodiment, the galvanic particulates are incorporated into wound dressings and bandages to provide galvanic electric therapy for healing enhancement and scar prevention. In one embodiment, the wound exudation fluid and/or wound cleansing solution serves to activate a galvanic particulate containing wound dressing/bandage to (i) deliver active agents pre-incorporated in the wound dressing/bandage and/or (ii) to generate electrochemically beneficial metal ions followed with delivery of the beneficial metal ions into the wound and/or (iii) treat the wound with therapeutic electric current which may increase blood circulation, stimulate tissue immune response, and/or suppress tissue inflammation, which may lead to accelerated healing and reduced scarring.

In one embodiment, the composition or product contains an active agent commonly used as for topical wound and scar treatment, such as topical antibiotics, anti-microbials, wound healing enhancing agents, topical antifungal drugs, anti-psoriatic drugs, and anti-inflammatory agents.

Examples of antifungal drugs include but are not limited to miconazole, econazole, ketoconazole, sertaconazole, itraconazole, fluconazole, voriconazole, clioquinol, bifoconazole, terconazole, butoconazole, tioconazole, oxiconazole, sulconazole, saperconazole, clotrimazole, undecylenic acid, haloprogin, butenafine, tolnaftate, nystatin, ciclopirox olamine, terbinafine, amorolfine, naftifine, elubiol, griseofulvin, and their pharmaceutically acceptable salts and prodrugs. In one embodiment, the antifungal drug is an azole, an allylamine, or a mixture thereof.

Examples of antibiotics (or antiseptics) include but are not limited to mupirocin, neomycin sulfate bacitracin, polymyxin B, 1-ofloxacin, tetracyclines (chlortetracycline hydrochloride, oxytetracycline-10 hydrochloride and tetrachcycline hydrochoride), clindamycin phsphate, gentamicin sulfate, metronidazole, hexylresorcinol, methylbenzethonium chloride, phenol, quaternary ammonium compounds, tea tree oil and their pharmaceutically acceptable salts and prodrugs.

Examples of antimicrobials include but are not limited to octenidine, salts of chlorhexidine, such as Iodopropynyl butylcarbamate, diazolidinyl urea, chlorhexidene digluconate, chlorhexidene acetate, chlorhexidene isethionate, and chlorhexidene hydrochloride. Other cationic antimicrobials may also be used, such as benzalkonium chloride, benzethonium chloride, triclocarbon, polyhexamethylene biguanide, cetylpyridium chloride, methyl, and benzothonium chloride. Other antimicrobials include, but are not limited to halogenated phenolic compounds, such as 2,4,4',-trichloro-2-hydroxy diphenyl ether (Triclosan); parachlorometa xylenol (PCMX); and short chain alcohols, such as ethanol, propanol, and the like.

Examples of anti-viral agents for viral infections such as herpes and hepatitis, include, but are not limited to, imiquimod and its derivatives, podofilox, podophyllin, interferon alpha, acyclovir, famcyclovir, valcyclovir, reticules and cidofovir, and salts and prodrugs thereof.

Examples of anti-inflammatory agents, include, but are not limited to, suitable steroidal anti-inflammatory agents such as corticosteroids such as hydrocortisone, hydroxyltriamcinolone alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinoide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, and salts are prodrugs thereof. In one embodiment, the steroidal anti-inflammatory for use in the present invention is hydrocortisone. A second class of anti-inflammatory agents which is useful in the compositions of the present invention includes the nonsteroidal anti-inflammatory agents.

Examples of wound healing enhancing agents include recombinant human platelet-derived growth factor (PDGF) and other growth factors, ketanserin, iloprost, prostaglandin $E_1$ and hyaluronic acid, scar reducing agents such as mannose-6-phosphate, analgesic agents, anesthetics, hair growth enhancing agents such as minoxadil, hair growth retarding agents such as eflornithine hydrochloride, antihypertensives, drugs to treat coronary artery diseases, anticancer agents, endocrine and metabolic medication, neurologic medications, medication for cessation of chemical additions, motion sickness, protein and peptide drugs.

In one embodiment, the galvanic particulates are used, with or without other antifungal active agents, to treat and prevent fungal infections. In another embodiment, the galvanic particulates are used, with or without other antibacterial active agents, to treat and prevent bacterial infections, including, but not limited to, infections of tissue injuries of intern or surface of the body due to surgical procedures such as acute wounds, and chronic wounds due to various illnesses (venous ulcers, diabetic ulcers and pressure ulcers).

In another embodiment, the galvanic particulates are used, with or without other antiviral active agents, to treat and prevent viral infections of the skin and mucosa, including, but not limited to, molluscum contagiosum, warts, herpes simplex virus infections such as cold sores, kanker sores and genital herpes.

In another embodiment, the galvanic particulates are used, with or without other antiparasitic active agents, to treat and prevent parasitic infectious, including, but not limited to, hookworm infection, lice, scabies, sea bathers' eruption and swimmer's itch.

In one embodiment, the particulates are administered to help treat ear infections (such as those caused by *streptococcus pneumoniae*), rhinitis and/or sinusitis (such as caused by *Haemophilus influenzae, Moraxella catarrhalis, Staphylococcus aureus* and *Streptococcus pneumoniae*), and strep throat (such as caused by *Streptococcus pyogenes*).

In one embodiment, the particulates are ingested by an animal (e.g., as animal feed) or a human (e.g., as a dietary supplement) to help prevent outbreaks of food borne illnesses (e.g., stemming from food borne pathogens such as *Campylobacter jejuni, Listeria monocytogenes*, and *Salmonella enterica*).

In one embodiment, the invention features a method of killing pathogens including drug resistant microorganisms by contacting the microorganism with a composition containing a galvanic particulate including a first conductive material and a second conductive material, wherein both the first conductive material and the second conductive material are exposed on the surface of the particulate, and wherein the difference of the standard potentials of the first conductive material and the second conductive material is at least about 0.2 V. In one embodiment, the particle size of said particulate is from about 10 nanometers to about 1000 micrometers, such as from about 1 micrometer to about 100 micrometers. In one embodiment, the second conductive material is from about 0.01 percent to about 10 percent, by weight, of the total weight of the particulate. In one embodiment, the drug resistant microorganism is a bacteria, such as MRSA and VRE. In one embodiment, the particulates are administered via a nasal spray, rinse solution, or ointment.

In one embodiment, the galvanic particulates can be used to reduce the visibility of skin facial wrinkles, reduce atrophy, or increase collagen stimulation. The galvanic particulates may be used either alone or in conjunction with other components well known in the art, such as subcutaneous fillers, implants, periodontal implants, intramuscular injections, and subcutaneous injections, such as bio-absorbable polymers. For example, the galvanic particulates may be used in conjunction with collagen and/or hyaluronic acid injections.

In another embodiment, the galvanic particulates can be incorporated into biodegradable scaffolds for tissue engineering and organ printing with techniques known in the art.

In another embodiment, the galvanic particles can be incorporated into aqueous gels for tissue adhesion prevention. For example, galvanic particulates in carboxyl methylcellulose aqueous solution or gel may be applied to a trauma site and surrounding tissue to reduce adhesion scar formation.

In another embodiment, the galvanic particles can be incorporated into aqueous gels for osteoarthritis treatment to eliminate or reduce pain and inflammation via intra-articular injection.

In another embodiment, the galvanic particles can be incorporated into an aqueous gel or an anhydrous gel for wound treatment to eliminate or reduce pain caused by inflammation, and to prevent or treat infection, to enhance healing rate and/or strength, and to reduce scarring.

Galvanic particulates may also be combined with an aqueous composition, such as aqueous gels or emulsions. The particulates may be mixed with an aqueous gel at the point of use. The galvanic particles may be present in the aqueous gel in the amount of about 0.01 weight % to about 0.5 weight %, and preferably about 0.01 weight % to about 0.25 weight %. In another embodiment, a mixture of galvanic particulates and suitable polymers in a dry form may be hydrated at the point of use. The suitable polymers include, but are not limited to carboxyl methylcellulose, hyaluronic acid, PEG, alginate, chitosan, chondroitin sulfate, dextran sulfate, and polymer blend and their salts thereof. Suitable aqueous solvents are water, physiological saline, phosphate-buffered saline, and the like. In another embodiment, the polymer(s) as gelling agent may be present in the aqueous gel in the amount of about 0.01 weight % to about 20 weight %, and preferably about 0.1 weight % to about 5 weight %.

In another embodiment, the galvanic particulates can be incorporated to the surface coating of a breast implant to improve the biocompatibility of implants and provide antimicrobial and anti-inflammatory benefits to eliminate or reduce capsular contracture.

In another embodiment, the medical devices of the present invention comprising galvanic particulates can be used with other energy-based medical devices and treatments to increase the therapeutic efficacy of either or both devices. The energy-based treatments include, but are not limited to, ultrasound device or therapy, magnetic treatment, electromagnetic device or therapy, radiofrequency treatment, thermal treatment (heating or cooling).

The novel medical devices of the present invention containing galvanic particulates can be used in various conventional surgical procedures, including but not limited to open and minimally invasive surgical procedures, for implanting medical devices and other implants such as wound closure following a surgical procedure, wound closure of traumatic injuries, catheter insertion, application of hemostats, stent implantation, insertion of vascular grafts and vascular patches, implanting surgical meshes, implanting bone implants, orthopedic implants and soft tissue implants, implanting bone grafts and dental implants, cosmetic surgery procedures, including implanting breast implants, tissue augmentation implants, and plastic reconstruction implants, inserting drug delivery pumps, inserting, or implanting diagnostic implants, implanting tissue engineering scaffolds, and other surgical procedures requiring long term or permanent implants. The devices of the present invention are implanted using surgical procedures in a conventional manner to obtain the desired result, and in addition, the use of the novel devices of the present invention provides for improved surgical outcomes by reducing infection and biofilm formation, suppressing inflammation and enhancing tissue repair and regeneration.

One skilled in the art will recognize that, both in vivo and in vitro trials using suitable, known and generally accepted cell and/or animal models are predictive of the ability of an ingredient, composition, or product to treat or prevent a given condition. One skilled in the art will further recognize that human clinical trials including first-in-human, dose ranging and efficacy trials, in healthy patients and/or those suffering from a given condition or disorder, may be completed according to methods well known in the clinical and medical arts.

The following examples are illustrative of the principles and practice of this invention, although mot limited thereto. Numerous additional embodiments within the scope and spirit of the invention will become apparent to those skilled in the art once having the benefit of this disclosure.

EXAMPLES

Example 1

Galvanic Particulate Preparation Based on Displacement Chemistry (a) In Pure Aqueous Media:

0.1% copper coated zinc galvanic particulates were manufactured by electroless plating of copper onto zinc powder. 10 g of ≤45-micron zinc powder was spread evenly onto a vacuum filter buchner funnel with a 0.22 micron filter. 5 g of copper acetate solution was then poured evenly onto the zinc powder, and allowed to react for approximately 30 seconds. A suction was then applied to the filter until the filtrate was completely suctioned out. The resulting powder cake was then loosed, and 10 g of deionized water was added and then suctioned off. 10 g of ethanol was then added to the powder under suction. The powder was then carefully removed from the filter system and allowed to dry in a desiccator.

(b) In Ethanol Containing Media:

0.1% copper coated zinc galvanic particulates were manufactured by electroless plating of copper onto zinc powder. 10 g of ≤45-micron zinc powder was weighed into a glass jar. 0.61% w/w copper acetate was dissolved into 200 proof ethanol. The resulting copper solution is a faint blue color. 5 g of copper acetate solution was then poured evenly onto the zinc powder, and allowed to react until the copper solution became clear. This reaction continued for approximately 48 hours at room temperature, when the solution turned clear. The composite was spread evenly onto a vacuum filter buchner funnel with a 0.22 micron filter. Vacuum suction was then applied to the filter until the filtrate was completely suctioned out. The resulting powder cake was then loosed, and 10 g of deionized water was added and then suctioned off. 10 g of ethanol was then added to the powder under suction. The powder was then carefully removed from the filter system and allowed to dry in a desiccator.

(c) In Pure Aqueous Media:

Approximately 0.1% copper coated magnesium galvanic particulates were manufactured by electroless plating of copper onto magnesium powder using the same method described in the Example 1(a), except substituting zinc powder with magnesium powder.

(d) In Pure Aqueous Media:

Approximately 0.1% iron coated magnesium galvanic particulates were manufactured by electroless plating of iron onto magnesium powder using same method described in the Example 1(a), except substituting zinc powder with magnesium powder and the copper lactate solution with a ferrous chloride solution.

Example 2

Coating Galvanic Particulate onto Hydrocolloid Substrate (a) Coating Process by Powder Sieving Deposition onto a Substrate:

First, the surface area of the self-adhesive hydrocolloid was measured and the amount of required galvanic particulates was calculated based on a 1.2 mg/cm$^2$ surface coating. The galvanic particulates of Example 1(a) were placed into a sieve #325 (45 micron) with the hydrocolloid sheet placed below the sieve. The sieve was gently shaken to produce an even coating of powders onto the hydrocolloid surface. A PET release liner was placed onto the galvanic particulate-coated hydrocolloid surface. The release liner is removed prior to use.

(b) Coating Process by Electrostatic Powder Deposition onto a Substrate:

Feasibility of coating the galvanic particulates onto a substrate with the electrostatic powder deposition technique was demonstrated using a commercial high voltage powder electrostatic coating system (HV Powder Coating System, purchased from Caswell, Inc., Lyons, N.Y.). The galvanic particulate and hydrocolloid materials, and sample preparation procedure were same as Example 2a. The voltage setting of the HV Powder Coating System was set at 45 kV, and compressed air was controlled at 15 psi (pounds-per-inch). The simple and high speed coating process resulted in a uniform coating of the galvanic powder on the hydrocolloid sheet was uniform.

Example 3

In Vitro Efficacy of Galvanic Particulates Against MRSA, Yeast and Bacteria

Galvanic particulates containing-agar discs were made by suspending the galvanic particulates from Example 1(a) in 2 ml of 47° C. sterile distilled water mixed with 8 ml of melted agar. The mixture was then poured into a 100×15 mm petri dish. The mixture solidified in the petri dish, and the galvanic particulates were immobilized and evenly distributed in the agar. Smaller agar discs were cut out front the galvanic particulate-containing agar with a sterile cork borer (inner D=12.2 mm), and used for further testing of the galvanic particulates.

The agar discs (D=12.2 mm, thickness=1.2 mm), containing the galvanic particulates at a concentration of either 0.5% or 1%, were placed on an agar plate surface inoculated with about 6 log CFU of indicator microorganisms. The plates were incubated at 37° C. for 24 hours. The zone of inhibition (distance in mm from edge of disc and edge of clear no growth zone) was measured with a digital caliper. Duplicate samples were used for this test. The results are depicted in Table 1.

TABLE 1

| Strains | Class | Zone of inhibition (mm) 0.5% | Zone of inhibition (mm) 1% |
|---|---|---|---|
| MRSA (Methicillin Resistant Staphylococcus aureus 33593) | Gram+ Bacteria | 1.3 | 2.9 |
| MRSE (Methicillin Resistant Staphylococcus epidermidis 51625) | Gram+ Bacteria | 1.8 | 3.6 |
| Candida albicans 10231 | Yeast | 0.9 | 2.0 |
| Pseudomonas aeruginosa 9027 | Gram− Bacteria | 0.4 | 1.2 |
| Corynebacterium aquaticum 14665 | Gram+ Bacteria | 1.0 | 1.4 |
| Corynebacterium jeikeium 43734 | Gram+ Bacteria | 1.9 | 3.3 |
| Staphylococcus haemolyticus 29970 | Gram+ Bacteria | 1.0 | 1.3 |
| Micrococcus lylae 27566 | Gram+ Bacteria | 1.0 | 2.3 |

* Results are means of duplicate samples

These results indicated that galvanic particulates were inhibitory against a wide-range of microorganisms, including antibiotic resistant bacteria (MRSA and MRSE), yeast (Candida albicans), and odor-producing species (Corynebacterium aquaticum, C. jeikelum, Staphylococcus haemolyticus, Micrococcus lylae, S. epidermidis). This in vitro efficacy shows the promises of using galvanic particulates for wound infection products, vaginal health products, and odor-reducing products.

Example 4

Efficacy of Galvanic Particulates Against MRSA and C. albicans Versus Metal Salt Controls Agar discs containing copper-zinc galvanic particulates from Example 1(a) or zinc acetate at a concentration of 0.1%, 0.5%, or 1% were exposed to about 6 log CFU of MRSA or C. albicans in saline in microwell plate and incubated at 37° C. and 200 rpm for 24 hrs. Plate count was performed to enumerate the viable microorganisms after the incubation. Log reduction was defined as the log difference of the inoculum before and after the incubation with the test articles (e.g., a log reduction of 6 for the inoculum of 6 log means all the inoculum were killed, and a log reduction of 3 for the inoculum of 6 log means 50% of the inoculum were killed). The results are set forth below in Table 2.

TABLE 2

| | LOG REDUCTION | | | |
|---|---|---|---|---|
| | C. albicans | | MRSA | |
| Concentration of test material | Galvanic particulates | Zinc Acetate | Galvanic particulates | Zinc Acetate |
| 0.10% | 6.5 | 2.2 | 2.4 | 1.7 |
| 0.50% | 6.5 | 2.9 | 6.7 | 3.2 |
| 1.00% | 6.5 | 4.7 | 6.7 | 5.1 |

Results show that the galvanic particulates have significantly more antimicrobial potency than zinc acetate, a metal salt control.

Example 5

Comparison of Antimicrobial Activity Against MRSA and VRE of Galvanic Particulates Versus Copper Metal and Zinc Metal Powders Agar discs with either galvanic particulates from Example 1(a) copper metal powders, zinc metal powders, or a control TSA only agar disc were inoculated with either 10e3 VRE or 10e5 MRSA. The zone of inhibition was evaluated. Results, reported in Table 3, indicated that 1% copper-zinc galvanic particulates inhibited growth of the inoculum completely, while the control, copper metal powder, and zinc metal powder discs showed no inhibition.

TABLE 3

| Test material | MRSA (10e3 inoculum) | MRSA (10e5 inoculum) |
|---|---|---|
| Control: TSA agar disc only | No inhibition | No inhibition |
| 1% w/w Copper metal | No inhibition | No inhibition |
| 1% w/w Zinc metal | No inhibition | No inhibition |
| 1% w/w Copper-zinc galvanic particulates | Inhibition | Inhibition |

Example 6

Comparison of Antimicrobial Activity Against *C. albicans* and MRSA of Galvanic Particulates Versus Copper Acetate and Zinc Acetate Zone of inhibition testing was performed on agar discs containing copper-zinc galvanic particulates from Example 1(a) at 0.5%, Zn acetate at 0.5%, and Cu acetate at 0.1%. The discs were placed on TSA agar surface, inoculated with about 6 log CFU of MRSA or *C. albicans*, and incubated at 37° C. for 24 hr. It was found that with both MRSA and *C. albicans*, the 0.5% galvanic particulates showed a significant, visible zone of inhibition. The 0.5% zinc acetate showed a smaller zone of inhibition, approximately one half the radius of the zone produced with the 0.5% galvanic particulates. The 0.1% copper acetate did not show any visible zone of inhibition with MRSA nor *C. albicans*.

Example 7

Comparison of Galvanic Particulates and Zinc Acetate and Copper Acetate by Agar Disc Microwell Assay Agar discs containing 0.1% copper coated zinc galvanic particulates from Example 1(a) or zinc acetate at 1% or copper acetate at 0.1% were exposed to about 6 log CFU of MRSA or *C. albicans* in saline in microwell plates, and incubated at 37° C., 200 rpm for 24 hr. Plate count was performed to enumerate the viable microorganisms after the incubation. Log reduction was defined as the log difference of the inoculum before and after the incubation with the test articles. The results are depicted below in Table 4.

TABLE 4

| | LOG REDUCTION | |
|---|---|---|
| | *C. albicans* | MRSA |
| 1% Galvanic Particulates | 6.4 | 6.7 |
| 1% Zinc Acetate | 4.7 | 5.1 |
| 0.1% Copper Acetate | 0.3 | 0.2 |

Example 8

Evaluation of the Long-Lasting, Sustained Efficacy of Galvanic Particulates Compared to Zinc Acetate Agars discs containing either galvanic particulates as described in Example 1(a) or zinc acetate at 1% were placed on TSA agar surface inoculated with about 6 log CFU of MRSA or *C. albicans* and incubated at 37° C. for 24 hr (day-1). After the incubation the agar discs were observed for zone of inhibition, then removed from the plates and placed onto a newly inoculated TSA plates with the same inoculum and incubated for 24 hr (day-2). It was found, that on day 1, both the galvanic particulate disc and zinc acetate disc produce a zone of inhibition against *C. albicans* and MRSA, and the zone produced by the galvanic particulates was larger than that of the zinc acetate disc. However, on day 2 only the disc containing the galvanic particulates demonstrated a visible zone of inhibition; the disc containing the zinc acetate did not show any inhibition. This demonstrates that the galvanic particulates have antimicrobial or inhibitory effects over sustained periods of time.

Example 9

Immunomodulation of Human T-Cell Cytokine Release Stimulated with PHA

The ability of the galvanic particulates from Example 1(a) to modulate immune responses was illustrated by their ability to reduce the production of cytokines by activated human T-cells stimulated with the T-cell receptor (TCR) activating agent phytohaemagglutinin (PHA) in the following assay.

Human T-cells were collected from a healthy adult male via leukopheresis. The T-cells were isolated from peripheral blood via Ficol gradient, and the cells were adjusted to a density of $1\times10^6$ cells/mL in serum free lymphocyte growth medium (ExVivo-15, Biowhittaker, Walkersville, Md.). Human T-cells were stimulated with 10 μg/mL PHA in the presence or absence of test compounds following published method (Hamamoto, Y., et al. Exp Dermatol 2:231-235, 1993). Following a 48-hour incubation at 37° C. with 5% $CO_2$, supernatant was removed and evaluated for cytokine content using commercially available multiplex cytokine detection kit. The results are depicted in Table 5.

TABLE 5

| | Cytokine Release | |
|---|---|---|
| Treatment | IL-2 (pmol/ml) | Percent (%) Reduction |
| Unstimulated | 2.8 ± 4.0 | N/A (Negative control) |
| PHA Stimulated | 563.2 ± 60.0 | N/A (Positive Control) |
| PHA + Copper Metal (100 ug/ml) | 498.9 ± 64.4 | 11.4% |
| PHA + Zinc Metal (100 ug/ml) | 456.8 ± 11.1 | 18.9% |
| PHA + Zinc Chloride (100 ug/ml) | 566.3 ± 20.6 | −0.6% |
| PHA + Copper (II) Acetate (100 ug/ml) | 312.9 ± 96.8 | 44.4% |
| PHA + Galvanic particulates (100 ug/ml) | 10.15 ± 3.5 | 98.2% |
| Hydrocortisone (Pos. Control 100 ug/ml) | 7.69 ± 5.64 | 98.6% |

(where IL-2 = Interleukin-2 (Cytokine)).

The galvanic particulates were found to be able to modulate the release of inflammatory mediators induced by T-cell stimulation. Furthermore, the anti-inflammatory activity was greater than that of copper metal powder, zinc metal powder, copper ion (Copper(II) Acetate), or zinc ions (Zinc Chloride) alone.

Example 10

Inhibition of NF-kB Activation

Nuclear Factor Kappa Beta (NF-kB) is a transcription factor that binds to the NF-kB binding site on the promoter region of pro-inflammatory genes, such as COX-2 and Nitric Oxide Synthase (iNOS) (Bell S, et al (2003) *Cell Signal*; 15(1): 1-7). NF-kB is involved in regulating many aspects of cellular activity, in stress, injury and especially in pathways of the immune response by stimulating synthesis of pro-inflammatory proteins, such as Cycloxygenase-2 (COX-2), thus leading to inflammation (Chun K S, t al. (2004) *Carcinogenesis* 25:445-454; Fenton M J (1992) *Int J Immunopharmacol* 14:401-411). NF-kB itself is induced by stimuli such as pro-inflammatory cytokines (e.g. TNF-alpha and IL-1beta), bacterial toxins (e.g. LPS and exotoxin B), a number of viruses/viral products (e.g. HIV-1, HTLV-1, HBV, EBV, and Herpes simplex), as well as pro-apoptotic and necrotic stimuli (e.g., oxygen free radicals, UV light, and gamma-irradiation). Inhibition of NF-kB activation is likely to reduce inflammation by blocking the subsequent signaling that results in transcription of new pro-inflammatory genes.

Solar ultraviolet irradiation activates the transcription factor NF-kB, inducing the production of matrix metalloproteinases that can lead to degradation of matrix proteins such as elastin and collagen. Inhibitors of NF-kB are likely to inhibit the subsequent signaling that results in the presence of MMPs in the dermal matrix, and the more of the pathway that is inhibited, the more likely there will be no induction of MMPs. Recently inhibition of the NF-kB pathway has shown to result in a subsequent induction in collagen synthesis (Schreiber J, et al. (2005) Surgery. 138:940-946). Thus, inhibition of NF-kB activation may also provide anti-aging benefits to skin by increasing collagen synthesis.

To evaluate the activity of galvanic particulates from Example 1(a) in blocking NF-kB activation, FB293 cells, a stable transfected human epithelial cell line containing the gene reporter for NF-kB was obtained from Panomics (Fremont, Calif.), were used. FB293 cells were plated at a density of $5\times10^4$ cells/mL in Dulbecco's modified Eagle's medium (DMEM) supplemented with 10% fetal bovine serum (Invitrogen, San Diego, Calif.). FB293 cells were stimulated with 50 ng/mL 12-O-tetradecanoylphorbol 13-acetate (TPA) (Sigma St Louis, Mo.) in the presence or absence of galvanic particulates. Following a 24 hour incubation at 37° C. with 5% $CO_2$, cells were lysed with 40 µl of reporter lysis buffer (Promega, Madison, Wis.). A 20-µl aliquot of the lysate was assayed using a luciferase assay kit (Promega) and counted for 10 seconds in a Lmax luminometer (Molecular Devices, Sunnyvale, Calif.) with the data represented as the relative light unit/second. Galvanic particulates were found to inhibit NF-kB activation as shown in Table 6.

TABLE 6

| | NF-kB Gene Reporter Activation (Luminescence) | Percent Inhibition |
|---|---|---|
| Untreated | 4.06 ± 0.6 | — |
| TPA (10 ng/ml) Stimulated | 28.46 ± 2.21 | — |
| TPA + Galvanic particulates (100 ug/ml) | 3.20 ± 1.98 | 88.7% |
| UV (10 kJ) Stimulated | 11.45 ± 1.89 | — |
| UV (10 kJ) + Galvanic particulates (100 ug/ml) | 5.51 ± 1.74 | 51.6% |

Galvanic particulates, thus, were found to substantially reduce NF-kB activation. This example demonstrates that galvanic particulates can modulate the production of inflammatory mediators, which contribute to inflammation of the skin. This example also demonstrates that galvanic particulates may also protect elastin and collagen fibers from damage and degradation that can lead to aging of the skin.

Example 11

Anti-Inflammatory Activity on Release of UV-Induced Pro-Inflammatory Mediators on Reconstituted Epidermis The effect of galvanic particulates was evaluated for topical anti-inflammatory activity on human epidermal equivalents. Epidermal equivalents (EPI 200 HCF), multilayer and differentiated epidermis consisting of normal human epidermal keratinocytes, were purchased from MatTek (Ashland, Mass.). These epidermal equivalents were incubated for 24 hours at 37° C. in maintenance medium without hydrocortisone. Equivalents were topically treated (2 mg/cm$^2$) with galvanic particulates (1 mg/ml) from Example 1(a) in 70% ethanol/30% propylene glycol vehicle 2 hours before exposure to solar ultraviolet light (1000 W-Oriel solar simulator equipped with a 1-mm Schott WG 320 filter; UV dose applied: 70 kJ/m$^2$ as measured at 360 nm). Equivalents were incubated for 24 hours at 37° C. with maintenance medium then supernatants were analyzed for IL-8 cytokine release using commercially available kits (Upstate Biotechnology, Charlottesville, Va.). The results are depicted in Table 7.

TABLE 7

| Treatment (Dose, as % w/v) | Mean +/− Std Dev of IL-1A Release (ng/ml) | Percent Inhibition of Skin Inflammation |
|---|---|---|
| Untreated, No UV | 223.5 ± 168.0 | — |
| UV (60 KJ), Vehicle Treated | 944.9 ± 205.3 | — |
| UV (60 KJ) + Galvanic particulates (1 mg/ml) | 477.7 ± 177.9** | 50.4% |

**Indicates significant difference from UV, Vehicle treated using a student's t-Test with significance set at P < 0.05.

Based on this example, topical application of galvanic particulates was able to significantly reduce the UV-stimulated release of inflammatory mediators. Therefore, galvanic particulates would be expected to provide an effective the anti-inflammatory benefit when applied to skin.

Example 12

Stimulation of Hydrogen Peroxide Production by Galvanic Particulates

Hydrogen peroxide ($H_2O_2$) has strong oxidizing properties and is therefore a powerful bleaching agent. Hydrogen peroxide is also an effective anti-bacterial, anti-fungal, and anti-viral compound that is even effective against methicillin resistant *Staphylococcus aureus* (MRSA) isolates (Flournoy D J, Robinson M C. (1990) Methods Find Exp Clin Pharmacol. 12:541-544). In addition, rinsing the oral cavity with a solution of hydrogen peroxide results in a significant reduction of aerobic and anaerobic bacteria in saliva (Matula C, Hildebrandt M, Nabler G. (1988) J Int Med Res.; 16:98-106). The reduction in bacteria in the oral cavity can help reduce the incidence of gingivitis.

Peroxides have been used in tooth whitening for more than 100 years, and hydrogen peroxide is one of the most commonly used active agents used in tooth whitening. (Li Y. (1996) Food Chem Toxicol. 34:887-904). Hydrogen peroxide is also an effective vasoconstrictor that can reduce the appearance of dark circles, and result in a skin whitening effect (Stamatas G N, Kollias N. (2004). J Biomed Opt. 9:315-322; Goette D K, Odom R B. (1977) South Med J. 70:620-622.).

The ability of galvanic particulates from Example 1(a) to induce the production of hydrogen peroxide was illustrated in the following assay. Human keratinocyte cells were seeded in assay plates at identical densities and incubated for 48 hours at 37° C. with 5% $CO_2$. To detect hydrogen peroxide production, keratinocytes were loaded for a 30-minute incubation period with 5 µM of the hydrogen peroxide-sensitive fluorescent probe 5-(and -6)-chloromethyl-2',7'-dichlorodihydrofluorescein diacetate, acetyl ester (CM-H2DCFDA, Invitrogen Carlsbad, Calif.). Cells were treated with galvanic particulates or zinc or copper metal powders alone over decreasing amounts of time. Treatment of control wells with 0.03% hydrogen peroxide served as a positive control. Hydrogen peroxide production was quantitated using a fluorescent plate reader set at wavelengths 485 excitation/530 emission. The results are depicted in Tables 8 and 9.

TABLE 8

| Compound | Baseline | 30 Minutes | 60 Minutes | 200 Minutes | 240 Minutes |
|---|---|---|---|---|---|
| Untreated | 42.3 ± 9.3 | 61.4 ± 13.9 | 88.1 ± 29.5 | 215.4 ± 125.8 | 243.9 ± 138.9 |
| Galvanic particulates (1%) | 77.3 ± 16.2 | 385.5 ± 98.6** | 726.6 ± 158.6** | 877.6 ± 186.3** | 842.2 ± 176.2** |
| $H_2O_2$ (0.03%) | 98.1 ± 4.4 | 416.6 ± 61.3** | 591.4 ± 82.7** | 1117.5 ± 153.8** | 1214.8 ± 149.7** |

**Indicates significant difference from baseline hydrogen peroxide levels at that timepoint using a student's t-Test with significance set at $P < 0.05$.

TABLE 9

| Compound | 60 Minutes |
|---|---|
| Copper Metal (0.1%) | 62.7 ± 4.27 |
| Zinc Metal (0.1%) | 76.4 ± 10.31 |
| Galvanic particulates (0.1%) | 190.5 ± 0.84 |

Based on this example, galvanic particulates were able to significantly induce the production of hydrogen peroxide. Furthermore, the production of hydrogen peroxide generated by galvanic particulates was substantially greater than that of copper metal powders or zinc metal powders alone. Therefore, galvanic particulates would be expected to provide an effective skin lightening, tooth whitening, and anti-bacterial activity when applied to skin.

Example 13

Anti-Fungal Effect

The galvanic particulates of Example 1(a) were evaluated in an in vitro onychomycosis model similar to that described in Yang, et al. *Mycopathologia* 148: 79-82, 1999. In order to simulate the foot onychomychosis, cow hoofs were used. Hoofs were punched into plates of 1.3 cm in diameter and then sterilized in an autoclave. The hoof plates were placed in sterile Petri dishes with their external face on sterile filter paper soaked with one of the antifungal preparations or with sterile water as controls. An agar block from a dermatophyte culture was implanted on the internal face. The whole apparatus was placed in a larger Petri dish containing sterile water to prevent dehydratation. After inoculation, the dermatophytes were moistened with 5 microliters of Sabouraud broth on a daily basis. The broth was deposited with a micro-pipette on the internal face of the hoof plate at the base of the agar block. The experimental material was placed on the hoof system at day 0, and the fungal growth was monitored daily, to determine the first day that the fungus grew through the nail. The date of appearance and amount of growth breakthrough was recorded. Hydrocolloid coated with 3.6 mg/cm$^2$ galvanic particulates was compared to untreated control. All samples were implicated 3 times.

The results are displayed in Table 10 and showed that the first breakthrough of fungal growth with the untreated control was 2 days, while the first breakthrough with the galvanic particulates was 5 days. This indicates that the galvanic particulates inhibit fungal growth or have anti-fungal activity.

TABLE 10

Growth of *T. rubrum* Through a Caw Hoof Plate as a Nail Plate Model

| Test Condition | Days for *T. rubrum* Growth Breakthrough the Hoof Plate |
|---|---|
| Zn—Cu Galvanic Particulate coated on Hydrocolloid (3.6 mg/cm$^2$) | 5 |
| Negative Control (No Treatment) | 2 |

Example 14

Controlling Rate of Reaction, Quality, and Activity of Galvanic Particulates

Changing the conditions of the metal plating of one metal onto another can affect the activity of galvanic particulates. The polarity of the reaction medium and presence of other agents such as completing and chelating agents, therefore, can be adjusted to create galvanic particulates of varying properties, including but not limited to coating thickness, coating density, coating pattern, and/or rate of reaction. The ability to control the rate of plating copper onto zinc powders is illustrated with the following example. The process described in Example 1(b) was performed with various types of 0.61% w/w copper acetate solutions outlined in Table 11, where the reaction time refers to the time it took for the copper to completely deposit onto the zinc powder, indicated by the copper salt solution changing from blue to clear.

TABLE 11

| % water | % ethanol | reaction time (hr) |
|---|---|---|
| 0 | 100 | 48.00 |
| 10 | 90 | 5.67 |
| 15 | 85 | 0.50 |
| 17 | 83 | 0.52 |
| 18 | 82 | 0.50 |
| 20 | 80 | 0.00 |

Based on this example, the rate of the coating reaction can be regulated by the polarity of the metal salt solution. Example 14 shows that the activity of the resulting galvanic particulates is affected by manufacturing conditions.

Example 15

Preparation of 35/65 (mol/mol) Poly(Epsilon-Caprolactone-co-Polyglycolide (PCL/PGA) Solution A 10% (w/v) 35/65 PCL/PGA solution was prepared by dissolving the polymer in 1,4-dioxane. 360 ml of 1,4-dioxane was transferred into a 500-ml flask and was then was preheated to 70° C. Forty grams of 35/65 PCL/PGA was slowly added into the solvent with stirring. The mixture was stirred for about 4 hours until a homogenous solution is formed. The polymer solution was filtered through a coarse ceramic filter and stored at room temperature. Solutions containing 7.5%, 5%, 2.5% and 1% 35/65 PCL/PGA were prepared following similar procedures.

Example 16

Preparation of Galvanic Particulate/Polymer Coated Polypropylene Mesh Using Cast-on-Mesh Process Polypropylene mesh at a size of 5"×6" was placed in a Teflon-coated metal tray (5"×6"). Ten milliliters of 7.5% (w/v) 35/65 PCL/PGA solution in 1,4-dioxane (prepared in Example 1) were mixed with 500 mg galvanic particulates 0.1% Cu on Zn prepared as described in Example 1b and placed into the tray with the mesh. The galvanic particulate suspension was quickly and evenly spread over the whole mesh. The coated mesh was air dried overnight and stored in nitrogen environment. Meshes coated with different amount of galvanic particulate were prepared following a similar procedure.

The coated mesh prototype was evaluated by scanning electron microscopy (SEM). The prototype sample was coated with a thin layer of carbon prior to SEM analysis to minimize charging of the sample. The carbon layer was applied using the Cressington 108C automatic carbon coater. The SEM analysis was performed using the JEOL JSM-5900LV SEM. Images were captured using the standard SEM SEI detector and the BEI (backscatter) detector. Overall the analysis indicates a different morphology for the top and bottom surfaces of the prototype (see FIG. 1). The morphology of side A shows the presence of the mesh adhered to a solid film-like underlayer. The observed morphology indicates that the galvanic particulate is uniformly distributed throughout the film-like underlayer of the prototype. The Images Indicate that the galvanic particles are well adhered to the sample, with some completely encapsulated within the polymer layer. The SEM images suggest some minor aggregation of the galvanic particles with a particle size diameter≤100 um, although the size of most of the bead-like particles ranged from 5 to 10 um. The morphology of side B shows a smooth film-like surface with the presence of the galvanic particulates uniformly distributed throughout the film-like layer.

Example 17

Preparation of Galvanic Particulates/Polymer Coated Polypropylene Mesh Using Hot Attachment Polypropylene meshes were coated with 35/65 PCL/PGA solution by dip-coating with 5%, 2.5% and 1% 35/65 PCL/PGA solutions that were prepared in Example 15. The coated mesh was air dried overnight in a fume hood. A polymer coated mesh at a size of 3×6 inches was placed on an 8" sieve and then stored in the nitrogen environment until use. Approximately 50 grams of galvanic particulate was transferred into a separate metal sieve (No. 635) and preheated to 120° C. in a nitrogen-purging oven about 5 minutes. Place the heated galvanic particulate loaded sieve above the mesh and manually shake the galvanic particulate loaded sieve and pass over the mesh area to allow the hot galvanic particulate to attach the mesh. The powder that did not attach to the mesh was removed by shaking the sieve with the mesh. The amount of galvanic particulate on the mesh was measured by weighting the polymer coated mesh before and after galvanic particulate coating. About 10, 7 & 5 mg/in$^2$ of particulates attachment were achieved for coated meshes with 5%, 2.5% and 1% PCL/PGA solutions respectively.

The prototype sample was coated with a thin layer of carbon prior to SEM analysis to minimize charging of the sample. The carbon layer was applied using the Cressington 108C automatic carbon coater. The SEM analysts was performed using the JEOL JSM-5900LV SEM. Images were captured using the standard SEM SEI detector and the BEI (backscatter) detector.

Figure 2:
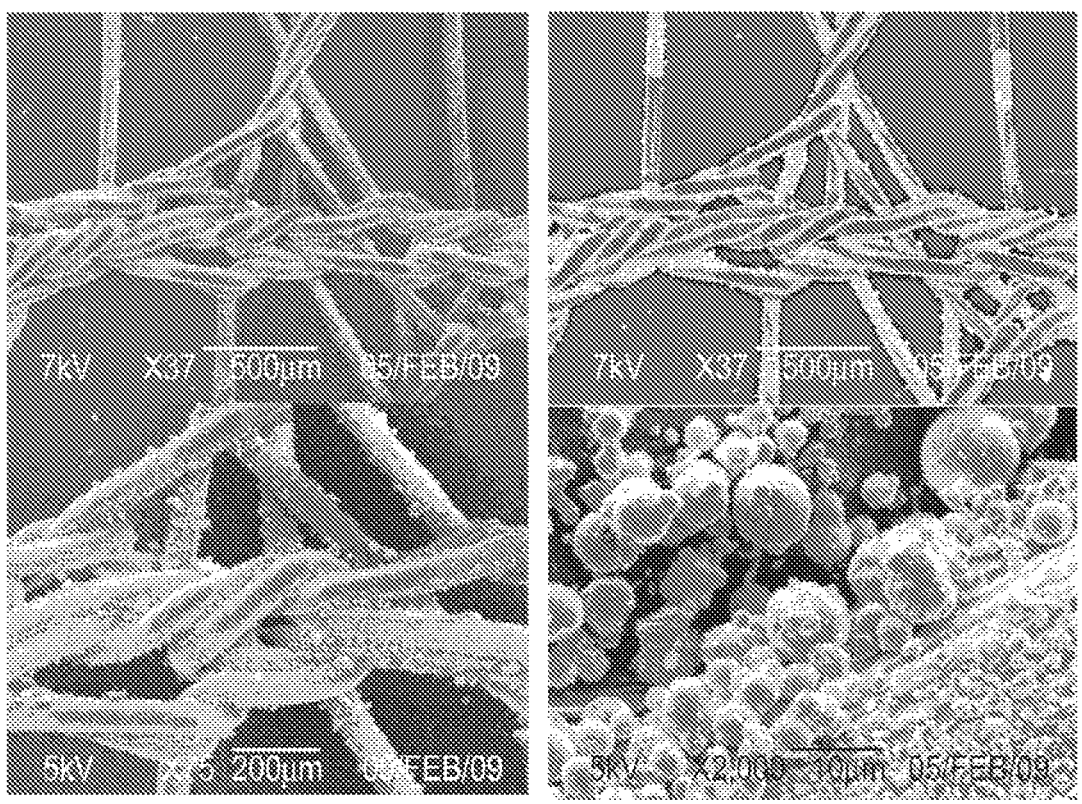
FIG. 2 is a SEM image of polypropylene mesh coated with Zn/Cu galvanic particulates using a dip coating process.

The SEM images of prototypes prepared using hot attachment process are shown in FIG. 2. Overall the analysis indicates an open mesh structure with a similar surface morphology for the top and bottom surfaces of the prototype. The SEM images show the presence of the galvanic particles attached to the polypropylene strands of the mesh structure. The galvanic particles appear to be highly concentrated within the strand-entangled regions of the mesh. The analysis also shows the galvanic particles adhered along the surface of the polypropylene strands throughout the mesh sample. The SEM images suggest some minor aggregation of the galvanic particles with a particle size diameter≤100 um, although the size of most of the bead-like particles ranged horn 5 to 10 um.

Example 18

Figure 3:
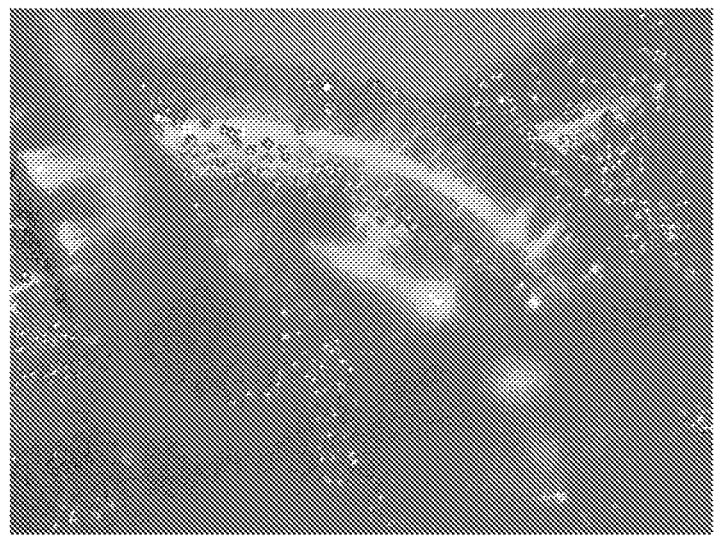
FIG. 3 is Light microscopic image of polypropylene mesh coated with Zn/Cu galvanic particulates using a microspray process.

Preparation of Galvanic Particulate/Polymer Coated Polypropylene Mesh Using Microspray In this experiment, a C-341 Conformal Coater with SC-300 swirl applicator from Asymtek (Carlsbad, Calif.) (a division of Nordson Corporation) was employed to atomize and deposit galvanic particulates onto a 3"×6" polypropylene mesh. The mesh sample was weighed and fixed to a 14"×17" platform inside the unit, approximately 1.5" under the spray head. Forty-five milliliters of 10% 35/65 PCL/PGA solution containing 575 milligrams of galvanic particulate was loaded into the nozzle. Air pressure on the spray unit was set to 50 PSI and nozzle translation speed was fixed at 5 inches per second. The mesh sample was lightly sprayed on both sides with the suspension, allowed to dry overnight, and weighed again to calculate the total mass of metal applied. Two additional mesh pieces were coated with heavier amounts of galvanic particulates. This was achieved by adjusting the nozzle opening to allow more fluid to pass through the spray head. The illustrations below capture the increasing dosage of galvanic particulate at 500× magnification (see FIG. 3).

Example 19

Anti-Microbial Activity of Galvanic Particulate Coated Mesh

Antimicrobial activity of galvanic particulate coated meshes prepared in Examples 16, 17, and 18 were evaluated using a BacT/ALERT system (BioMerieux, Inc., Durham, N.C.). The fully automated BacT/ALERT system was used to detect *Staphylococcus aureus* (SA) growth over a 14-day study at 35° C. by continuous monitoring of $CO_2$ production using an optical colorimetric sensory system. Briefly, each of the prototype samples of approximately 3"×6" were aseptically rolled into a 3" lengthwise bundle using sterile forceps and transferred into a BacT/ALERT sample bottles containing 9 mL of aerobic casein and soy based broth culture medium. Upon transfer into the BacT/ALERT sample bottles, the prototype galvanic particulate coated mesh samples, designated in Table 12 below, were uncoiled to rest against the interior walls of each sample bottle. One mL aliquots of SA were inoculated into each sample bottle to produce a total media volume of 10 mL containing approximately $2 \times 10^5$ CFU/mL for antimicrobial efficacy testing. The 1 mL SA inoculums were taken from a BacT/ALERT sample bottle designated SA-1 dilution, produced by inoculating 1 mL from an overnight SA BacT/ALERT culture bottle into a new BacT/ALERT bottle containing 40 mL of media. The sample bottle designated SA-1 dilution was then serially diluted by inoculating 1 mL into new BacT/ALERT sample bottles containing 40 mL of media to produce additional SA positive control sample bottles designated SA-2, -3 and -4 dilutions respectively. The BacT/ALERT time-to-detection growth results of these SA positive control sample bottles are shown in Table 14 below. The absence of SA growth in the galvanic particulate coated mesh BacT/ALERT samples shown in Table 12 demonstrate the antimicrobial activity of the galvanic particulate coated mesh prototype samples. This inhibition of SA growth can be attributed to the galvanic electricity and/or electrochemically generated species generated by the galvanic particulate coatings.

TABLE 12

| Sample # | Polymer Concentration (%) | ePowder Density (mg/Inch$^2$) | Positive Growth Time-to-detection (Days) |
|---|---|---|---|
| Cast ePowder Suspension | | | |
| 1 | 7.5 | 15.2 | Neg. |
| 2 | 7.5 | 3.1 | Neg. |
| 3 | 7.5 | 0.75 | Neg. |
| Dip-Coating and Post heated ePowder attachment | | | |
| 1 | 5 | 18.2 | Neg. |
| 2 | 5 | 19.7 | Neg. |
| 3 | 1 | 8.3 | Neg. |
| 4 | 1 | 7.4 | Neg. |
| Microspray | | | |
| 1 | 10 | 1.7 | Neg. |
| 2 | 10 | 7.8 | Neg. |
| 3 | 10 | 21.1 | Neg. |
| Positive Controls | | | |
| SA-1 dilution | NA | NA | 0.16 |
| SA-2 dilution | NA | NA | 0.26 |
| SA-3 dilution | NA | NA | 0.44 |
| SA-4 diluiton | NA | NA | 0.62 |

Example 20

Anti-Inflammatory Activity on Release of UV-Induced Pro-Inflammatory Mediators on Reconstituted Epidermis The effect of galvanic particulate coated mesh prepared in Example 17 and having galvanic particulate in the amount of about 7 mg/in$^2$ was evaluated for anti-inflammatory activity on human epidermal equivalents. Epidermal equivalents (EPI 200 HCF), multilayer and differentiated epidermis consisting of normal human epidermal keratinocytes, were purchased from MatTek (Ashland, Mass.). Upon receipt, epidermal equivalents were incubated for 24 hours at 37° C. in maintenance medium without hydrocortisone. A circular biopsy punch was used to create a 8 mm diameter sample for testing both the galvanic particulate coated mesh and mesh that was uncoated. The coated mesh and uncoated mesh were placed on top of the skin equivalents respectively for 2 hours before exposure to solar ultraviolet light (1000 W-Oriel solar simulator equipped with a 1-mm Schott WG 320 filter; UV dose applied: 70 kJ/m$^2$ as measured at 360 nm). Equivalent were incubated for 24 hours at 37° C. with maintenance medium then supernatants were analyzed for IL-1a cytokine release using commercially available kits (Upstate Biotechnology, Charlottesville, Va.). Results are shown in Table 13 below.

TABLE 13

| Treatment (Dose, as % w/v) | Mean +/− Std Dev of IL-1A Release (ng/ml) | Percent Inhibition of Skin Inflammation |
|---|---|---|
| Untreated, No UV | 1.18 ± 0.18 | — |
| UV (60 KJ), Uncoated Mesh | 306.83 ± 80.79 | — |
| UV (60 KJ) + Galvanic Particulate coated mesh | 181.41 ± 53.05** | 50.4% |

**Indicates significant difference from UV + Uncoated Mesh treated using a student's t-Test with significance set at $P < 0.05$.

Based on the example application the galvanic particulate coated mesh was able to significantly reduce the UV-stimulated release of inflammatory mediators. Therefore, galvanic particulate coated mesh would be expected to provide an effective anti-inflammatory benefit.

Example 21

Preparation of Galvanic Particulates Loaded Carboxyl Methylcellulose (CMC) Gel

A 2.5% (w/v) aqueous solution of carboxylmethylcellulose (CMC) (7HFPH, Aqualon Chemical Company, Wilmington, Del.) in phosphate buffer was prepared and sterilized via autoclaving. Galvanic particles containing 99.25% zinc and 0.75% copper were sterilized by gamma irradiation at a dosage of 25 KGy. A CMC gel containing 1 mg/ml and 0.25 mg/ml galvanic particles was prepared by mixing the sterile CMC gel and galvanic particles in the same day of animal testing Example 22

Rabbit Double Uterine Horn (DUH) Model Study

The goal of the study was to evaluate the efficacy of test articles applied at the site of injury at the end of surgery on the reduction of adhesion formation over 21-day period.

As shown is table 14, sixty female New Zealand White rabbits, 2.4-2.7 kg. were used in the study. Ten rabbits were randomized into six treatment groups (table below) prior to initiation of surgery. Rabbits were anesthetized with a mixture of 55 mg/kg ketamine hydrochloride and 5 mg/kg Rompum intramuscularly. Following preparation for sterile surgery, a midline laparotomy was performed. The uterine horns were exteriorized and traumatized by abrasion of the serosal surface with gauze until punctate bleeding developed. Ischemia of both uterine horns was induced by removal of the collateral blood supply. The remaining blood supply to the uterine horns was the ascending branches of the utero-vaginal arterial supply of the myometrium. At the end of surgery, no treatment, vehicle control (4 mL), and CMC gels containing galvanic powder described in Example 22 were administered. The horns were then returned to their normal anatomic position and the midline incision was sutured with 3-0 Vicryl suture.

TABLE 14

| Group Number | Treatment | Animal Number |
|---|---|---|
| Surgical Control | Surgery Only | 10 |
| Vehicle Control | Vehicle Control (2.5% CMC gel) | 10 |
| Treatment 1 | 1 mg/ml galvanic particulates in 2.5% CMC gel | 10 |
| Treatment 2 | 0.25 mg/ml galvanic particulates in 2.5% CMC gel | 10 |

After 21 days, the rabbits were euthanized and the percentage of the area of the horns adherent to various organs was determined. In addition, the tenacity of the adhesions was scored. The results are shown in Table 15. It was demonstrated that there were no biocompatibility issues or adverse clinical observations noted post-surgery; no inflammation was observed at necropsy; and galvanic particulates loaded CMC gels showed a reduction of adhesion at both non surgical and surgical sites.

TABLE 15

| Group | Percentage Adhesion Free | # Score ≤1.5/Total |
|---|---|---|
| Surgical Control | 0.0 | 0/10 |
| Vehicle Control | 21.25 | 3/10 |
| Treatment 1 | 41.25 | 7/10 |
| Treatment 2 | 36.25 | 9/10 |

Example 23

Preparation of Galvanic Particulate-Coated Cured Silicone Elastomer

This example describes how a silicone breast implant may be coated with the galvanic particulates. A 12"×12" bi-layer sheet of uncured/cured silicone elastomer (0.012" thick) was coated with 0.1% Cu/Zn galvanic particulates. The top layer of the elastomer sheet is catalyzed, but uncured. The bottom layer of the sheet is fully cured. This material is referred to as "vulc/unvulc sheeting". A 100 ppi (pores per square inch) 12"×12" sheet of polyurethane foam is folded over on itself and approximately ½ tsp of galvanic particulates was placed onto the top surface of the foam. The foam is gently tapped to let the galvanic particulates distribute evenly into the foam. The unvulc/vulc sheeting is placed on an aluminum pan vulc (cured) side down and the corners taped to the pan to prevent movement of the sheet. The folded foam containing the distributed galvanic particulates is swept back-and-forth across the unvulc (uncured) surface to leave a thin, fairly even layer of galvanic particulates. A fresh sheet of foam is then folded and the folded edge is used to sweep the powdered surface until no additional powder is removed. A Teflon tube is then used to roll the coated surface two to three times to increase the adhesion of the remaining powder to the unvulc (uncured) surface. The resulting coated silicone elastomer sheet is then placed on an aluminum tray and cured for 2 hours at 325° F. The final sheet is then packaged and dry-heat sterilized.

Example 24

Preparation of Galvanic Particulates in Gel (a) 1 percent (w/v) aqueous solution of carboxylmethylcellulose (CMC) (7HFPH, Aqualon Chemical Company, Wilmington, Del.) in phosphate buffer pH 7.4 was prepared and sterilized via autoclaving for use as the gel carrier. 100 mg of 0.75 percent copper coated zinc galvanic particulates were weighed and loaded into a sterile 12 ml syringe and capped. Galvanic particulates in the syringe were gamma irradiated at a dosage of 25 kGy. Following sterilization, galvanic particulates were mixed with 10 ml of sterile CMC also loaded in a sterile 12 ml syringe by connection with a 3-way luer lock valve and using aseptic sterile techniques. Galvanic particulates and CMC were mixed 30 times to form a 10 mg/ml galvanic particulate in CMC gel. This 10 mg/ml galvanic particulate/CMC solution was further diluted to 1 mg/ml by adding 1 ml of 10 mg/ml galvanic particulate/CMC to an additional 9 ml of sterile CMC gel. A sterile 3-way valve was used to transfer both 10 mg/ml galvanic particulate/CMC and sterile CMC into fresh 1.2 ml sterile syringes connected by a 3-way luerlock valve. The 1 mg/ml galvanic particulate/CMC gel was obtained after the solutions were mixed 30 times. A 0.25 mg/ml galvanic particulate/CMC solution was obtained by further diluting the 1 mg/ml galvanic particulate/CMC. 2.5 ml of 1 mg/ml galvanic particulate/CMC was added to an additional 7.5 ml of sterile CMC gel. A sterile 3-way valve was used to transfer both 1 mg/ml galvanic particulate/CMC and CMC into fresh 12 ml sterile syringes. The solutions were mixed 30 times to provide the 0.25 mg/ml galvanic particulate/CMC gel.

(b) A hyaluronic acid (HA) gel sold under the tradename ORTHOVISC (Anika Therapeutics, Inc.) and distributed by DePuy Mitek, Inc. was used as the carrier. 20 mg of 0.75 percent copper coated zinc galvanic particulates were weighed and loaded into a sterile 3 ml syringe and capped. Galvanic particulates in the syringe were gamma irradiated at a dosage of 25 kGy. Following sterilization, galvanic particulates were mixed with 2 ml of sterile HA by connection with a 3-way luer lock valve and using aseptic sterile techniques. Galvanic particulates and HA were mixed 30 times to form a 1.0 mg/ml galvanic particulate/HA gel. This 10 mg/ml galvanic particulate/HA solution was further diluted to 1 mg/ml galvanic particulate/HA by adding 0.2 ml of 10 mg/ml galvanic particulate/HA to an additional 1.8 ml of sterile HA gel. A sterile 3-way valve was used to transfer both 10 mg/ml galvanic particulate/HA and HA into fresh 3 ml sterile syringes connected/by a 3-way luer lock valve. The solution was mixed 30 times to provide a 1 mg/ml galvanic particulate/HA gel. A 0.25 mg/ml galvanic particulate/HA solution was obtained by further diluting the 1 mg/ml galvanic particulate/HA. 0.5 ml of 1 mg/ml galvanic particulate/BA was added to an additional 1.5 ml of sterile HA gel. A sterile 3-way valve was used to transfer both 1 mg/ml galvanic particulate/HA and HA into fresh 3 ml sterile syringes connected by a 3-way luer lock valve and mixed 30 times to provide the 0.25 mg/ml galvanic particulate/HA.

Example 25

Efficacy of Galvanic Particulate in CMC Gel on Pain Relief in a Rat Monoarthritis Model Induced by Complete Freund's Adjuvant (CFA)

Figure 4:
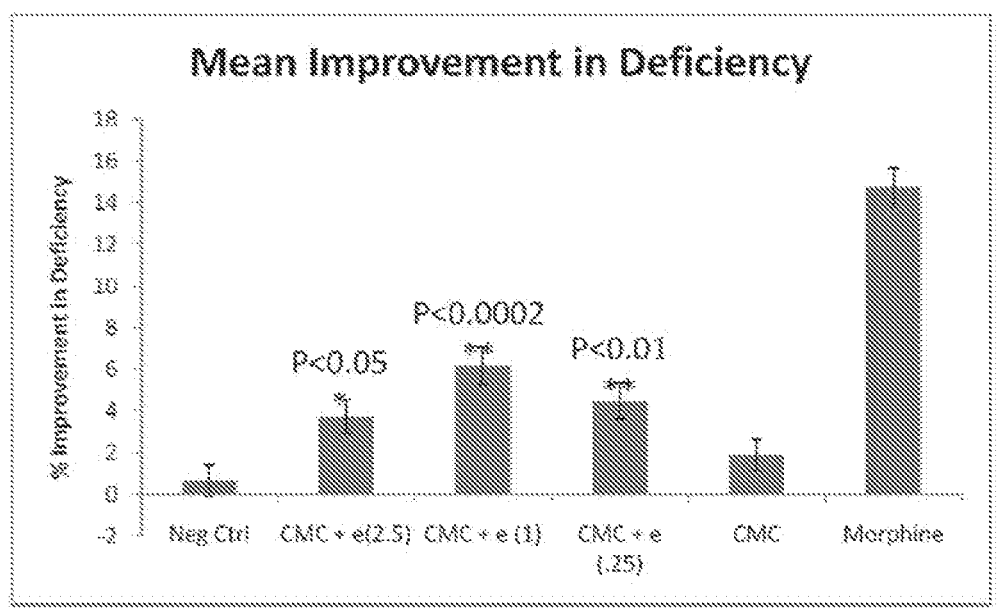
FIG. 4 is a graph showing the Mean improvement in weight bearing deficiency for galvanic particulates in a carboxylmethylcellulose (CMC) gel carrier.

Pain relief of galvanic particulates was evaluated in a rodent Complete Freund's Adjuvant (CFA) model of inflammatory joint pain. Ninety male albino Wistar rats sold under the tradename SPRAGUE DAWLEY (CD[Crl:CD(SD)] strain), approximately 8 weeks old were randomized into 6 groups, each having 15 animals. The efficacy of galvanic particulates was tested in 3 groups: 2.5 mg/ml galvanic particulate/CMC, 1 mg/ml galvanic particulate/CMC, and 0.25 mg/ml galvanic particulate/CMC (each prepared on the same day the treatment was administered as described in Example 1). The other 3 groups included negative control, vehicle control (1 percent carboxyl methylcellulose (CMC)) and morphine as positive control for pain relief. Prior to injection of an induction article, the animals were anesthetized to effect with isoflurane. Monoarthritis was induced on day 0 on the animals of all groups by a 50 microliter injection of Complete Freund's adjuvant (CFA) containing *M. tuberculosis* at 2 mg/ml into the right ankle articular cavity. On day 5, 50 microliters of the treatment group (vehicle and test articles) were administered intra-articularly into the right ankle joint. The effect of galvanic particulates on pain relief was evaluated with an incapacitance test for weight bearing difference between the injected ankle and its counter lateral ankle. Briefly, the weight borne on each hind paw was measured in triplicates employing a latency period of 5 s and the percentage weight borne on the affected right limb expressed. The improvement of weight bearing percent from the day of treatment was calculated for each time point by subtracting the percentage of weight bearing on day 4 from those on days 7, 8, 10, 11, 13 and 14. The mean improvement in deficiency was then obtained by averaging the improvement of weight bearing percent from all time points in each treatment group (FIG. 4).

All three concentrations of galvanic particulates in CMC gel showed a statistically significant improvement over the negative control and the CMC gel alone with 1 mg/ml galvanic particulate/CMC exhibiting the greatest improvement. These data demonstrate that the galvanic particulate/CMC gel was useful in relieving joint pain in the arthritis condition.

Example 26

Efficacy of Pain Relief and Anti-Inflammatory Effect of Galvanic Particulates in Two Different Formulations in a Rat Monoarthitis Model Induced by Complete Freund's Adjuvant (CFA)

One hundred five male albino Wistar rats sold under the tradename SPRAGUE DAWLEY (CO[Crl:CD(SD)] strain), approximately 8 weeks old were divided into seven groups with N of 15 animals in each group. The seven groups included: Group 1, no treatment (Negative); Group 2, Vehicle 1 [1 percent carboxylmethylcellulose (CMC) gel]; Group 3, 1 mg/ml galvanic particulates/CMC; Group 4, 0.25 mg/ml galvanic particulates/CMC; Group 5, Vehicle 2 (hyaluronic acid gel); Group 6, 1 mg/ml galvanic particulates/HA; and Group 7, Morphine, the positive control for the study. The galvanic particulate in gel formulations were prepared as described in Example 1 on the same day the treatment was administered. Prior to injection of an induction article, the animals were anesthetized to effect with isoflurane. On day 1, all rats were administered, via intra-articular injection into the right ankle joint space, Complete Freund's Adjuvant (CFA) at 2 mg/mL *M. tuberculosis* to induce monoarthritis in the injected ankle. On day 5 post CFA injection when significant arthritis was induced, one treatment group of 15 rats received nothing as the Negative control group. A 50 microliter dose of vehicle (CMC or HA) alone or galvanic particulates in gel treatment groups was given to the same joint cavity as the CFA. The last group of 15 rats was administered the positive control article, morphine sulphate, at a dose level of 3 mg/kg. The positive control article was administered once daily via subcutaneous injection at a dose volume of 2 mL/kg/day.

The pain level and efficacy of treatments on reduction of pain were assessed through weight beating measurements of the hind limbs on Days −1, 1, 4, 7, 8, 10, 11, 13, 14, 19, 22, 25, and 28 as described in Example 25. Modulation of inflammatory reaction by various treatments was also evaluated by paw volume measurement on day 29, the end of study. The paw volume was measured for both hind limbs using a plethysmometer. Swelling of the right hind paw was calculated by subtracting the volume of left hind paw and the difference was plotted.

Figure 5:
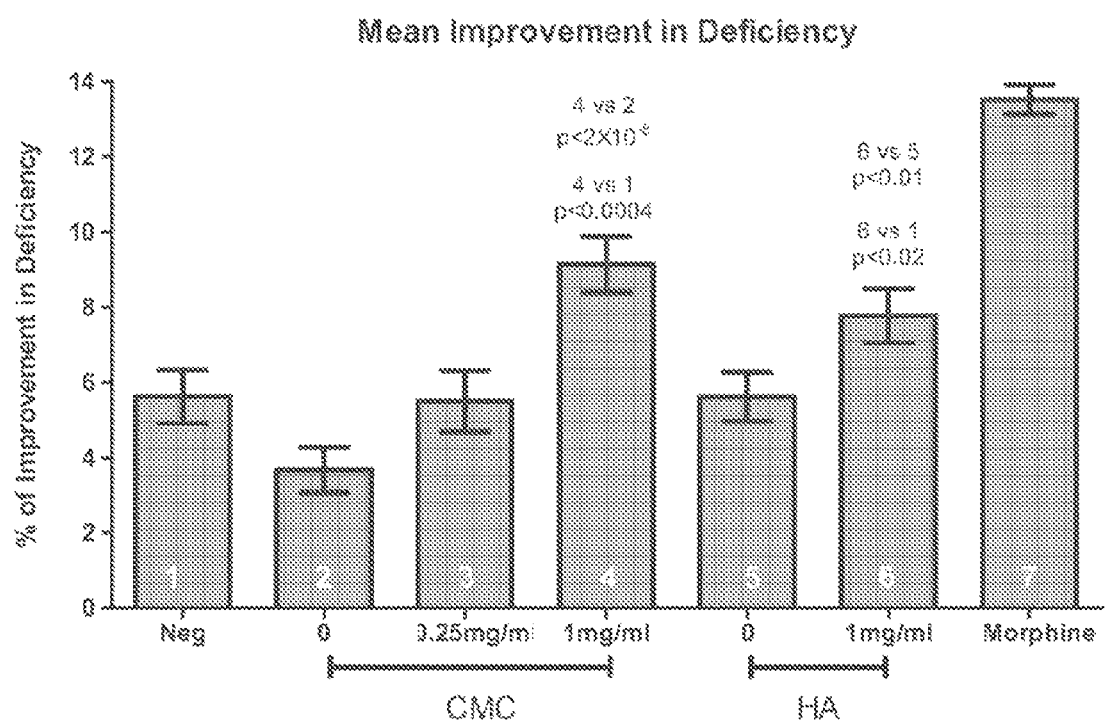
FIG. 5 is a graph showing the Mean improvement in weight bearing deficiency for galvanic particulates in a 1% CMC gel carrier or an hyaluronic acid (HA) gel carrier.

The 1 mg/ml galvanic particulates in both CMC (Group 4) and HA (Group 6) gel had a statistically significant improvement in weight bearing deficiency of the affected right hind limb when compared with Negative (Group 1) and either vehicle controls (Groups 2 and 5), although not as potent as the Morphine treated group (Group 7, FIG. 5). The results of 1 mg/ml galvanic particulates in CMC (Group 4) are consistent with those in Example 23, confirming that galvanic particulates in a gel earlier are useful for pain relief.

Figure 6:
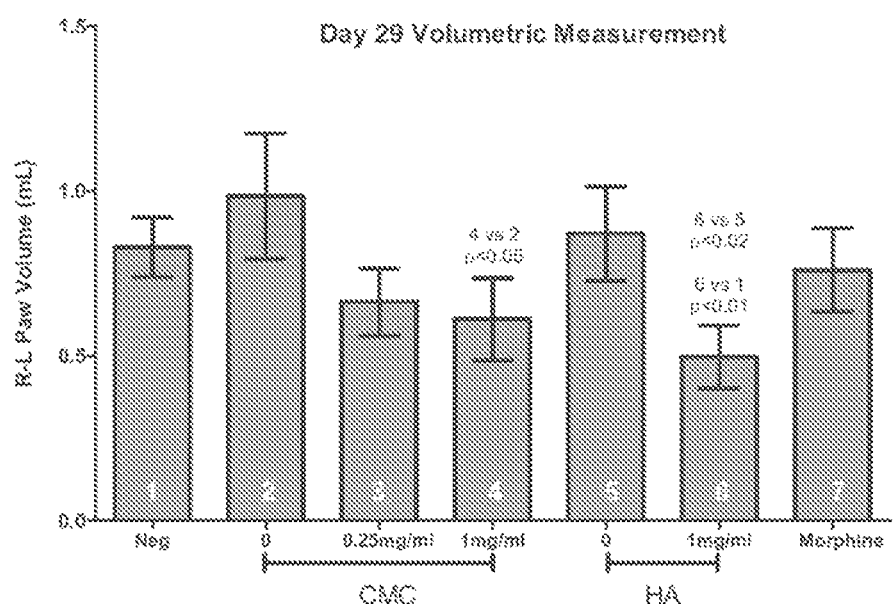
FIG. 6 is a graph showing the paw volume reduction after treatment with galvanic particulates in a 1% CMC gel carrier or an HA gel carrier.

With respect to the paw volume measurements, galvanic particulates in a gel carrier demonstrated an improvement in right hind limb swelling. The 1 mg/ml galvanic particulates in HA (Group 6) had a statistically significant improvement over either Negative (Group 1), vehicle control (Group 5), or Morphine treated group (Group 7) (FIG. 6). The 1 mg/ml galvanic particulates in CMC (Group 4) also showed a marginal improvement when compared to its corresponding vehicle group (Group 2). The reduction in swelling of the affected right hind limbs indicated that galvanic particulates in a gel carrier, especially in HA, are useful in reducing inflammatory reactions, thus pain level, consistent with improvement in weight bearing of the affected hind limb as described above in this example as well as in Example 25.

Example 27

Efficacy of Pain Relief and Anti-Inflammatory Effect of Galvanic Particulate in HA Formulation in a Rat Monoarthitis Model Induced by Complete Freund's Adjuvant (CFA)

A total of ninety male albino Wistar rats sold under the tradename SPRAGUE DAWLEY (CD[Crl:CD(SD)] strain), approximately 8 weeks old were randomized to 6 Groups with 15 rats in each group. All animals were anesthetized to effect with isoflurane prior to injection of the induction article. Animals in all group were administered the induction article once on Day 0 via intra-articular injection into the right ankle joint space at a dose volume of 50 microliters Complete Freund's Adjuvant (CFA) with 2 mg/mL *M. tuberculosis*. One treatment group of 15 male rats served as the negative control and was untreated (Group 1). Three treatment groups of 15 male rats were administered 50 microliters of the test articles (2.5, 1, or 0.25 mg/ml galvanic particulates in HA gel carrier prepared as described in Example 1 on the day the treatment was administered, Groups 3,4, and 5). An additional group of 15 animals served as the vehicle control HA and received 50 microliters of the vehicle (Group 2). The test articles and vehicle were administered once on Day 5 via intra-articular injection into the right ankle joint space. A treatment group of 15 male rats was administered the positive control article morphine sulphate at a dose level of 3 mg/kg (Group 7), once daily, prior to the functional measurements. Weight bearing measurements were conducted on Days −1, 1, 4, 7, 8, 10, 11, 13, 14, 19, 22, 25, and 28. Paw volumes were measured and recorded on Day 29, the last day of the study.

Figure 7:
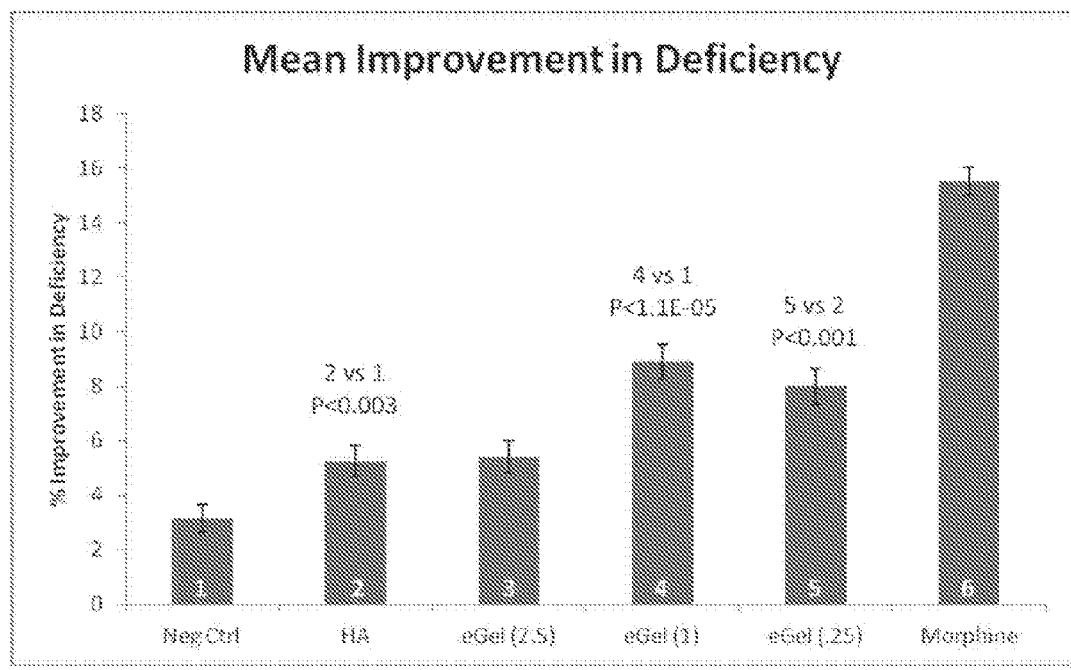
FIG. 7 is a graph showing the Mean improvement in weight bearing deficiency for galvanic particulates in an HA gel carrier.

Weight bearing measurements of the hind limbs were made prior to the arthritis induction and at intervals beginning at Day 1 after the arthritis induction and on days as indicated above. The mean improvement of weight bearing deficiency data demonstrate that galvanic particulates at both 1 (Group 4) and 0.25 (Group 5) mg/ml in HA had a statistically significant improvement in pain reduction in the affected paw (FIG. 7), which was consistent with the results in both Examples 25 and 26.

Figure 8:
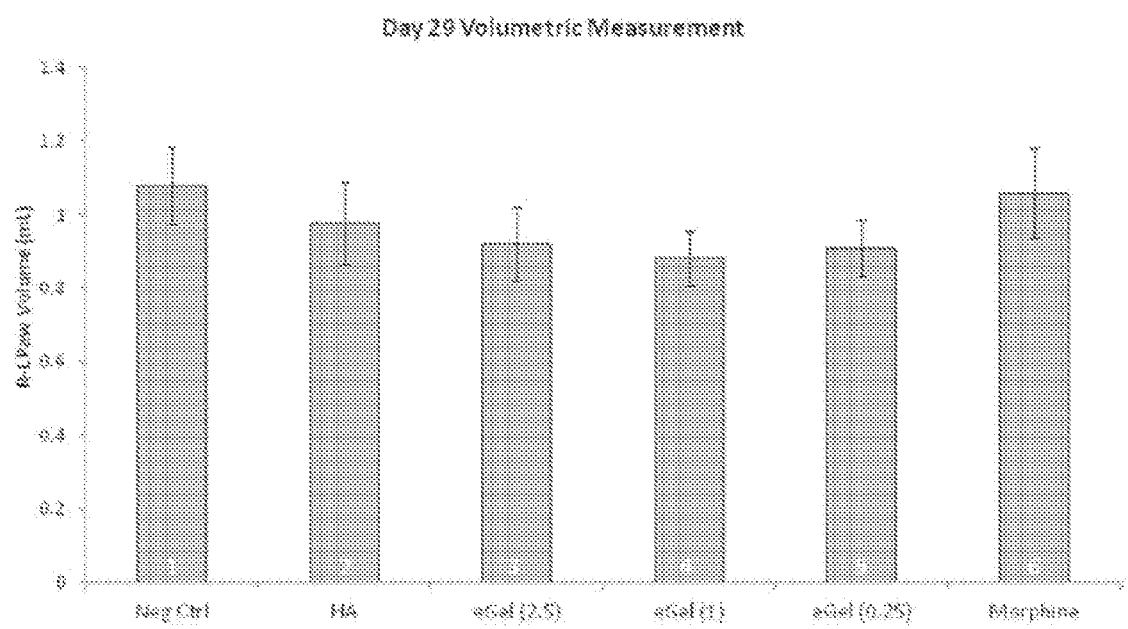
FIG. 8 is a graph showing the paw volume reduction after treatment with galvanic particulates in an HA gel carrier.

After CFA induction, all animals exhibited swelling in the right hind limb starting from day 5 (data not shown). Galvanic particulates in the gel carrier showed a trend of improvement in the reduction of swelling when compared to negative control (Group 1), HA carrier (Group 2), and Morphine (Group 6) (FIG. 8) although not statistically significant. This result, consistent with the observation in Example 26, suggests that galvanic particulates in a gel carrier may be useful in the reduction of swelling in osteoarthritis.

Example 28

Recovery of Galvanic Particulates in Injection Syringe after Gel Mixing Preparation In a separate study, the recovery of galvanic particulates alter mixing with HA gel following the procedure as illustrated in Example 24 was measured using Inductively Coupled Plasma Mass Spectrometry (ICP) to obtain actual dose delivered in a CFA preclinical study as described in Example 27. Briefly, galvanic gel prepared at 0.25, 1, and 2.5 mg/ml was sampled and analyzed with TCP method to determine the actual concentration of galvanic particulates in HA gel through detecting elemental Zn ions. The concentrations of galvanic particulates analyzed with this method showed 1.37±0.44 mg/ml for prepared 2.5 mg/ml galvanic particulate gel [(55±17)% recovery], 0.48±0.14 mg/ml for prepared 1 mg/ml gel [(48±14)% recovery] and 0.15±0.01 mg/ml for prepared 0.25 mg/ml gel [(60±0.06)% recovery]. Since the prepared galvanic gel at both intended dosage of 0.25 and 1 mg/ml are effective in pain relief as shown in Example 27, the effective dose of galvanic particulates could be as low as 0.15 mg/ml.

Although this invention has been shown and described with respect to detailed embodiments thereof, it will be understood by those skilled in the art that various changes in form and detail thereof may be made without departing from the spirit and scope of the claimed invention.

We claim:

1. A method of relieving joint pain in the arthritic condition comprising the steps of providing a composition comprising a galvanic particulate and an aqueous gel, and delivering the composition into a joint, wherein the aqueous gel comprises a carboxylmethylcellulose
    wherein the galvanic particulate comprises a first conductive material and a second conductive material, wherein both said first conductive material and said second conductive material have surfaces which are at least partially exposed, wherein the particle size of said particulate is from about 10 nanometers to about 100 micrometers, wherein the second conductive material comprises from about 0.01 percent to about 10 percent, by weight, of the total weight of said particulate, and wherein the difference of the standard potentials of the first conductive material and the second conductive material is at least about 0.2 V, and
    wherein the composition comprises 0.25 mg/ml to 1 mg/ml carboxymethylcellulose.

2. The method of claim 1 wherein the first conductive material is selected from the group consisting of zinc and magnesium, and the second conductive material is selected from the group consisting of copper and silver.

3. The method of claim 1 wherein delivering the composition into a joint consists of injecting the composition intra-articularly into the joint.

* * * * *